United States Patent
Choi et al.

(10) Patent No.: US 12,409,107 B2
(45) Date of Patent: Sep. 9, 2025

(54) GLASS IONOMER CEMENT COMPOSTION FOR DENTAL PURPOSES AND METHOD FOR PREPARING THE SAME

(71) Applicant: HASS CORPORATION, Gangneung-si (KR)

(72) Inventors: Sung Hwan Choi, Seoul (KR); Jae Sung Kwon, Seoul (KR); Jin Kee Hong, Seoul (KR); Ji Young Seo, Seoul (KR); Ji Yeong Kim, Seoul (KR); Woo Jin Choi, Seoul (KR)

(73) Assignee: HASS CORPORATION, Gangneung-si (KR)

( * ) Notice: Subject to any disclaimer, the term of this patent is extended or adjusted under 35 U.S.C. 154(b) by 912 days.

(21) Appl. No.: 17/566,147

(22) Filed: Dec. 30, 2021

(65) Prior Publication Data

US 2022/0233409 A1 Jul. 28, 2022

(30) Foreign Application Priority Data

Jan. 28, 2021 (KR) ........................ 10-2021-0012404

(51) Int. Cl.
| | |
|---|---|
| *A61K 6/889* | (2020.01) |
| *A61K 6/60* | (2020.01) |
| *A61K 6/71* | (2020.01) |
| *A61K 6/77* | (2020.01) |
| *A61K 6/898* | (2020.01) |

(52) U.S. Cl.
CPC ................ *A61K 6/889* (2020.01); *A61K 6/60* (2020.01); *A61K 6/71* (2020.01); *A61K 6/77* (2020.01); *A61K 6/898* (2020.01)

(58) Field of Classification Search
None
See application file for complete search history.

(56) References Cited

U.S. PATENT DOCUMENTS

| | | | | |
|---|---|---|---|---|
| 5,063,257 | A | * | 11/1991 | Akahane ................. A61K 6/77 522/120 |
| 2005/0020720 | A1 | * | 1/2005 | Dickens ................. A61K 6/887 523/117 |
| 2006/0205838 | A1 | | 9/2006 | Velamakanni et al. |
| 2019/0151204 | A1 | | 5/2019 | Akiyama et al. |
| 2019/0380919 | A1 | | 12/2019 | Shimosoyama et al. |
| 2021/0000698 | A1 | | 1/2021 | Uchida et al. |

FOREIGN PATENT DOCUMENTS

| | | |
|---|---|---|
| JP | 2007-524635 A | 8/2007 |
| JP | 6371580 B2 | 8/2018 |
| JP | 2019-167334 A | 10/2019 |

(Continued)

OTHER PUBLICATIONS

Lee et al ("Improvement in the Microbial Resistance of Resin-Based Dental Sealant by Sulfobetaine Methacrylate Incorporation", Polymers, (2020), 12, 17-17, pp. 1-11) (Year: 2020).*

(Continued)

*Primary Examiner* — Michael Forrest
(74) *Attorney, Agent, or Firm* — Sughrue Mion, PLLC

(57) ABSTRACT

The present specification provides a dental glass ionomer cement (GIC) composition comprising a zwitterionic material and a glass ionomer cement, and a method of preparing the same.

14 Claims, 16 Drawing Sheets

(56) References Cited

FOREIGN PATENT DOCUMENTS

| JP | 2020-152730 | A | 9/2020 |
|---|---|---|---|
| KR | 10-2019-0048876 | A | 5/2019 |
| KR | 10-2020-0031882 | A | 3/2020 |
| KR | 10-2020-0115256 | A | 10/2020 |
| KR | 10-2184281 | B1 | 11/2020 |

OTHER PUBLICATIONS

Machine Translation for KR 20190048876 (Year: 2019).*
Lee et al., "Bioactive resin-based composite with surface pre-reacted glass-ionomer filler and zwitterionic material to prevent the formation of multi-species biofilm", Dental Materials, Jul. 16, 2019, vol. 35, No. 9, pp. 1331-1341 (11 pages total).
Nicholson et al., "Enhancing the Mechanical Properties of Glass-Ionomer Dental Cements: A Review", Materials, May 31, 2020, vol. 13, No. 11, pp. 1-14 (14 pages total).
Extended European Search Report issued Jun. 30, 2022 in European Application No. 22153322.7.
Marwa A. Tawfik et al., "Evaluation of Modified Glass Ionomer Cements With Protein Repellent and Nanostructured Antibacterial Properties in Prevention of Enamel Demineralization. An In Vivo Study", Apr. 2019, 959:964, vol. 65.
Dohyun Kim, et al., "Incorporation of zwitterionic materials into light-curable fuoride varnish for bioflm inhibition and caries prevention", Scientific Reports, (2019) 9:19550.
Se Young Park, et al., "Synergetic Effect of 2-Methacryloyloxyethyl Phosphorylcholine and Mesoporous Bioactive Glass Nanoparticles on Antibacterial and Anti-Demineralisation Properties in Orthodontic Bonding Agents", Nanomaterials 2020, 10, 1282; doi: 10.3390.
Ning Zhang, et al., "Antibacterial and protein-repellent orthodontic cement to combat biofilms and white spot lesions", J Dent. Author manuscript; available in PMC Dec. 1, 2016.
Temmy Pegarro Vales, et al., "Development of Poly(2-Methacryloyloxyethyl Phosphorylcholine)-Functionalized Hydrogels for Reducing Protein and Bacterial Adsorption", Materials 2020, 13, 943; doi:10.3390.
Tayseer Maaly, "Evaluation of Antibacterial Activity and Compressive Strength of Protein Repellent Nanostructured Orthodontic Modified Glass Ionomer Cement", Current Science International, Dec. 30, 2018, vol. 7, Issue 4, ISSN: 2077-4435, pp. 808-813 (6 pages).
Jae-Sung Kwon et al., "Durable Oral Biofilm Resistance of 3D-Printed Dental Base Polymers Containing Zwitterionic Materials", International Journal of Molecular Sciences, Jan. 3, 2021, vol. 22, No. 417, pp. 1-13 (13 pages).
Utkarsh Mangal et al., "Bio-Interactive Zwitterionic Dental Biomaterials for Improving Biofilm Resistance: Characteristics and Applications", International Journal of Molecular Sciences, Nov. 29, 2020, vol. 21, No. 9087, pp. 1-21 (21 pages).

* cited by examiner

FIG. 2A
| Group | Glass Ionomer Cement (GIC), wt% | 2-Methacryloyloxyethyl Phosphorylcholine (MPC), wt% | Sulfobetaine Methacrylate (SB), wt% |
|---|---|---|---|
| Control | 100 | 0 | 0 |
| Example 1 | 97 | 3 | 0 |
| Example 2 | 97 | 0 | 3 |
| Example 3 | 97 | 1.5 | 1.5 |
FIG. 2B
2-Methacryloyloxyethyl Phosphorylcholine
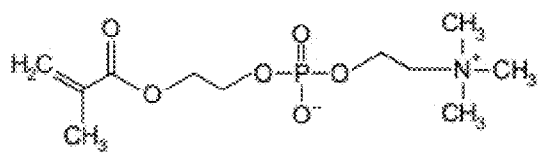
Sulfobetaine Methacrylate
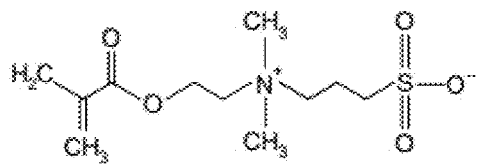

(a)

(b)

(a)

(b)

(a)

(b)

(c)

GLASS IONOMER CEMENT COMPOSTION FOR DENTAL PURPOSES AND METHOD FOR PREPARING THE SAME

CROSS-REFERENCE TO RELATED APPLICATION

This application claims under 35 U.S.C. § 119(a) priority to and benefit of Korean Patent Application No. 10-2021-0012404 filed on Jan. 28, 2021, the entire contents of which are incorporated herein by reference.

BACKGROUND

(a) Technical Field

The present invention relates to a dental composition, and more specifically, to a dental glass ionomer cement composition and a method of preparing the same.

(b) Background Art

Dental cement is a material used in a variety of dental treatments such as permanent or temporary restorations, bonding of metallic restorations, sealing of root canals, cheese packs or guards, and the like. Although dental cement cannot guarantee its permanence, it is used in more than half of the dental restorative procedures because of its economical and easy-to-use advantages. These dental cements may be classified into glass ionomer cement, zinc phosphate cement, zinc silicate cement, zinc oxide-eugenol cement, polycarboxylate cement, resin cement, silicate cement, calcium hydroxide cement, and the like, depending on the component.

Among them, glass ionomer cement (GIC) has an excellent fluoride-free ability capable of doing a bacteriostatic action and suppressing the occurrence of caries, a thermal expansion coefficient similar to that of dentin, a small shrinkage during curing, and an excellent bonding strength with tooth structure, small microleakage, and the like.

On the other hand, these dental cements must have the durability to withstand temperature changes caused by cold and hot food, acidity changes caused by acidic and alkaline foods, severe pressure changes due to chewing force, and the characteristics of the human oral cavity that are always wet with saliva.

Furthermore, bacterial plaque and tartar may adhere to most dental cements if mechanical cleaning such as brushing is neglected. In addition, a biofilm may be easily formed due to a humid oral environment, and the formed biofilm may further cause the formation of aggregation of bacteria and fungi.

Accordingly, there is a demand for a material that has an appropriate hardness to withstand changes in temperature, acidity, pressure and humidity in the oral cavity, is difficult to propagate bacteria and fungi, and has high stability without dissolution of substances that adversely affect the human body, such as allergies and endocrine disruption.

However, the above-mentioned glass ionomer cements have limitations in clinical application due to disadvantages such as low abrasion resistance, low tensile strength, drying sensitivity, difficulty in polishing, long curing time, aesthetically opacity (chalk), and the like.

The background technology of the invention has been prepared to facilitate understanding of the invention. It should not be construed as an admission that the matters described in the background technology of the invention exist as prior art.

SUMMARY OF THE INVENTION

On the other hand, in order to overcome the limitations of the above-described glass ionomer cements, studies have been made to increase the mechanical properties by using an additive. More specifically, in order to overcome the disadvantages of conventional glass ionomer cements, a resin-modified glass ionomer (RMGI) cement in which a composite resin is mixed has been developed. However, when the cavity is large, it also has aesthetic limitations such as light opacity, limited color tone, color stability after the procedure, and the like, and has a lower bonding strength compared to composite resin. Furthermore, since the resin-modified glass ionomer cement is also sensitive to dehydration, it still has clinical limitations, as it has to be polished under water after being stabilized by leaving it as it is for 10 minutes or more after initial curing.

In addition, the glass ionomer cement was used by mixing metal alloys such as silver-tin, silver-palladium, and silver-titanium to improve mechanical properties as well as the above-mentioned resin, but the bioactivity was impaired with an unpleasant metallic color change.

After all, the conventional glass ionomer cement only improved mechanical properties, but did not improve bioactivity, that is, mineralization such as precipitation of apatite or hydroxyapatite related to bone formation, and thus, did not provide the fundamental therapeutic and preventive effect of teeth.

On the other hand, the inventors of the present invention have noted that a zwitterionic material is used with various dental materials to contribute to the antifouling effect of blocking the adsorption of proteins and bacteria. Accordingly, the inventors of the present invention have recognized that, when the zwitterionic material was also used in GIC, it could provide an improved antifouling effect even in GIC, and thus, studied a new dental composition that may effectively prevent infection by bacteria as a restorative material together with GIC.

As a result, the inventors of the present invention have found that, when the zwitterionic material was used together with GIC, the blocking effect on adsorption of surface proteins and bacteria was increased compared to when GIC is used alone. Furthermore, the inventors of the present invention have found that the zwitterionic material could contribute not only to the aforementioned antifouling effect, but also to the killing of various microorganisms including bacteria, and recognized that this is an ion release effect by the zwitterionic material.

At this time, the inventors of the present invention have found that when the bonds between bridging oxygens (BOs) present inside the GIC was broken due to the difference in the density of charges between different zwitterionic materials, the ratio of non-bridging oxygens (NBOs) was increased. Furthermore, it has been also found that the above-mentioned ion release effect was increased by a high NBO ratio.

Accordingly, in addition to the zwitterionic material, the inventors of the present invention recognized that when the difference in the density of charges can be caused inside the GIC without convergence of the net charge to zero, the ion release effect of the GIC could be improved.

As a result, in addition to the zwitterionic material, the inventors of the present invention have found that various charged materials such as hydroxylapatite (HAp), glass fiber, silver-tin alloy, zirconia ($ZrO_2$), alumina ($Al_2O_3$), titania ($TiO_2$) nanoparticles, and bioactive glass could improve the ion release effect of the GIC.

In addition, the inventors of the present invention have further noted that certain degradable releasing compositions could form chemical bonds with bone due to the release of ions such as $Na^+$, $Si^{4+}$, and $Ca^{2+}$.

After all, the inventors of the present invention have found that when one or more zwitterionic materials or a variety of materials that could be included with zwitterionic materials to cause a difference in the density of charges while not having a net charge of zero were used with the GIC, the ion release of the GIC was improved, and by a cascading mechanism, the bioactivity was increased and the formation of tooth enamel could be increased.

Thus, the problem to be solved by the present invention is to provide a glass ionomer cement that is a dental restoration material capable of improving the biofouling effect and antibacterial properties of teeth, by including one or more zwitterionic materials having a specific ratio, or one or more materials selected from the group consisting of hydroxylapatite (HAp), glass fiber, silver-tin alloy, zirconia ($ZrO_2$), alumina ($Al_2O_3$), titania ($TiO_2$) nanoparticles and bioactive glass.

The problems of the present invention are not limited to the above-mentioned problems, and other problems that are not mentioned above will be clearly understood by those skilled in the art from the following description.

According to one embodiment of the present invention, the present invention provides a dental glass ionomer cement (GIC) composition comprising a zwitterionic material and a glass ionomer cement.

In this case, the term "zwitterionic material" as used herein may refer to an ionic material having an acidic and basic atomic group in a molecule, wherein both groups are in an ionized state at the same time and have both negative and positive charges. Furthermore, this zwitterionic material may not have a net charge of zero depending on the functional groups and their bridging carbons.

According to a feature of the present invention, the zwitterionic material may have a content of about 1 to 5 wt % based on the total mass of the dental glass ionomer cement composition.

According to another feature of the present invention, the present invention may comprise one or more selected from the group consisting of hydroxylapatite (HAp), glass fiber, silver-tin alloy, zirconia ($ZrO_2$), alumina ($Al_2O_3$), titania ($TiO_2$) nanoparticles, and bioactive glass, together with the zwitterionic material described above. However, the present invention is not limited thereto, and the material included in the dental glass ionomer composition may comprise not only a zwitterionic material, but also a combination of two or more materials that may cause a difference in the density of charges while not having a net charge of zero.

In this case, the zwitterionic material, hydroxylapatite (HAp), glass fiber, silver-tin alloy, zirconia ($ZrO_2$), alumina ($Al_2O_3$), titania ($TiO_2$) nanoparticles and bioactive glass as described above may mean a modifier. For example, the zwitterionic material used in a method of preparing the dental glass ionomer cement composition according to one embodiment of the present invention is a modifier capable of increasing the release of internal ions and strengthening physical properties, by blocking the bonds between bridging oxygens (BOs) present inside the GIC using a difference in the density of charges in the zwitterionic material to increase the ratio of non-bridging oxygens (NBOs). Accordingly, the modifier used in a method of preparing the dental glass ionomer cement composition according to one embodiment of the present invention may further comprise, in addition to the zwitterionic material described above, various materials capable of increasing the ratio of NBOs inside the GIC as it has a localized charge density.

According to other feature of the present invention, the zwitterionic material and one or more selected from the group consisting of hydroxylapatite (HAp), glass fiber, silver-tin alloy, zirconia ($ZrO_2$), alumina ($Al_2O_3$), titania ($TiO_2$) nanoparticles and bioactive glass may not have a net charge of zero. That is, as the partial charges of the functional groups included in each added material are unbalanced, the offset partial charges become non-homogeneous, so that bonds between BOs may be more effectively blocked.

According to another feature of the present invention, the zwitterionic material may comprise one or more selected from the group consisting of 2-methacryloyloxyethyl phosphorylcholine (MPC), sulfobetaine methacrylate (SB), 1,2-dimyristoyl-sn-glycero-3-phosphatidylcholine (DMPC), 3-dimethylsulfoniopropanoate (DMSP), trigonelline, ectoine, betaine, N-(2-methacryloyloxy)ethyl-N,N-dimethylammonio propanesulfonate (SPE), N-(3-methacryloylimino)propyl-N,N-dimethylammonio propanesulfonate (SPP), carboxybetaine methacrylate (CBMA), and 3-(2'-vinyl-pyridinio)propanesulfonate (SPV), and preferably MPC and SB. When the MPC and SB are included together, the ratio of MPC and SB may be, but is not limited to, about 1 MPC:about 1 SB based on weight, and various zwitterionic materials other than MPC and SB may be set and used in various ratios. For example, the ratio of MPC to SB may be set between 1:3 to 3:1. In this case, when two or more zwitterionic materials are included in the specific ratio described above, as the density of charges in the zwitterionic material is more localized, the released amount of ions included in the GIC may be further improved, and accordingly, bioactivity may be further enhanced.

According to another feature of the present invention, the GIC may have a content of about 95 to 99 wt % based on the total mass of the dental glass ionomer cement composition. In this case, as the dental glass ionomer cement composition includes about 95 to 99 wt % of GIC based on the total mass, it still maintains the inherent properties and physical properties of GIC without change, and may further include an additional effect by the modifier.

According to another feature of the present invention, the GIC may comprise, but is not limited to, an acid-reactive inorganic filler powder and a liquid containing a poly acid, and may be a combination of a hydraulic powder and a liquid such as water.

According to another feature of the present invention, the acid-reactive inorganic filler powder is an inorganic filler that chemically reacts in the presence of an acidic component, and when an acidic liquid is mixed, carboxyl group ions (—COOH) released through an acid-base reaction may chemically bond with $Ca^{2+}$ in the tooth structure, so that it is possible to have high adhesion to the teeth. For example, the acid-reactive inorganic filler may comprise one or more selected from the group consisting of, but not limited to, basic metal oxides, metal hydroxides, aluminosilicate glass, fluoroaluminosilicate glass, and calcium fluoroaluminosilicate glass, and all materials containing silica may be included.

On the other hand, in the dental glass ionomer cement composition of the present invention, a preferred acid-reactive inorganic filler may be calcium fluoroaluminosilicate glass, which may have particles of about 13 to 19 µm. Furthermore, the calcium fluoroaluminosilicate glass may be synthesized by one or more selected from the group consisting of, but not limited to, $SiO_2$, $Al_2O_3$, $CaF_2$, $Na_3AlF_6$, $AlF_3$, and $AlPO_4$.

According to another feature of the present invention, in the dental glass ionomer cement composition of the present invention, the basic metal oxide of the acid-reactive inorganic filler may include one or more selected from the group consisting of barium oxide, strontium oxide, calcium oxide, magnesium oxide, and zinc oxide, and the metal hydroxide may include one or more selected from the group consisting of calcium hydroxide, magnesium hydroxide, and strontium hydroxide.

According to another feature of the present invention, in the dental glass ionomer cement composition of the present invention, the acid-reactive inorganic filler powder may further comprise barium glass to increase radiopacity.

According to another feature of the present invention, the liquid containing the poly acid may refer to a polymer having a plurality of acidic repeating units, wherein a functional group representing acidity may be attached to the backbone of each polymer, and may be a homopolymer or a copolymer. That is, the liquid containing the poly acid included in the dental glass ionomer cement composition of the present invention may include not only poly acids, but also all polymers that may release carboxyl group ions (—COOH) through an acid-base reaction with an acid-reactive inorganic filler powder to cause chemical bonding with $Ca^{2+}$ in the tooth structure, for example, the poly acid may comprise one or more selected from the group consisting of: homopolymers of acrylic acid, methacrylic acid, itaconic acid, maleic acid, glutaconic acid, aconitic acid, citraconic acid, mesaconic acid, fumaric acid, or tiglic acid; and copolymers thereof; and a copolymer of maleic acid and ethylene.

According to another feature of the present invention, the liquid containing the poly acid may further include, but is not limited to, itaconic acid as an additive for improving physical properties in addition to the above-described acidic polymer, and may include all of a variety of materials for lowering the viscosity, that is, capable of preventing gelation by blocking intermolecular hydrogen bonding.

Furthermore, the liquid containing the poly acid included in the dental glass ionomer cement composition of the present invention may further include a complexing agent as well as the above-described additive for improving physical properties. For example, the complexing agent that may be contained in the liquid included in the dental glass ionomer cement composition of the present invention may further include one or more selected from the group consisting of, but not limited to, tartaric acid, citric acid, ethylene diamine tetraacetic acid (EDTA), salicylic acid, mellitic acid, dihydroxy tartaric acid, nitrilotriacetic acid (NTA), 2,4- and 2,6-dihydroxybenzoic acid, phosphono carboxylic acid, and phosphono succinic acid.

According to another feature of the present invention, the dental glass ionomer cement composition may further comprise one or more selected from the group consisting of, is not limited to, a stabilizer, a flame retardant, an antistatic agent, a softener, a modifier, a filler, a fluorescence brightening agent, a lubricant, an inclusion reducing agent, a polycondensation catalyst, a defoamer, an emulsifier, a thickener, and a perfume.

According to another feature of the present invention, the dental glass ionomer cement composition may comprise one or more functional groups selected from the group consisting of C=O, C—N, $N^+(CH_3)_3$, POCH, S=O symmetric, and S=O asymmetric.

According to one embodiment of the present invention, the present invention provides a method of preparing a dental glass ionomer cement composition, comprising the steps of: mixing about 1 to 5 wt % of zwitterionic material in a liquid of glass ionomer cement (GIC) based on the total mass of the dental glass ionomer cement composition, and mixing the liquid of GIC in which the zwitterionic material is mixed, and a powder of GIC.

According to a feature of the present invention, in the step of mixing the zwitterionic material in the liquid of GIC, the zwitterionic material may preferably comprise the MPC and the SB, more preferably comprise the MPC to the SB in a weight ratio of, but not limited to, 1:3 to 3:1 based on the weight, and when one or more various zwitterionic materials are included, they may be included in a mixture in various ratios.

According to another feature of the present invention, the present invention may further comprise a step of comprising one or more selected from the group consisting of hydroxylapatite (HAp), glass fiber, silver-tin alloy, zirconia ($ZrO_2$), alumina ($Al_2O_3$), titania ($TiO_2$) nanoparticles, and bioactive glass in the step of mixing the zwitterionic material in the liquid of GIC.

Hereinafter, the present invention will be described in more detail through examples. However, these examples are only for illustrating the present invention, and thus, the scope of the present invention should not be construed as being limited by these examples.

The present invention may overcome the limitations associated with the antibacterial prevention and treatment of the conventional dental composition composed of GIC alone, by providing a dental glass ionomer cement composition comprising a zwitterionic material.

More specifically, the present invention may provide improved antifouling effect and bioactivity compared to when GIC is used alone, by including one or more zwitterionic materials or modifiers together.

That is, the present invention may block and prevent dental caries by providing anti-fouling action and corresponding antibacterial activity when applied to restoration treatment of teeth, and furthermore, has the effect of providing a dental restoration material that prevents an inflammatory reaction due to an infection caused by microorganisms such as bacteria and has excellent antibacterial activity.

In particular, the present invention may be excellent in the effect of preventing the biological adhesion of pathogenic bacteria such as *Candida albicans, Actinomyces naeslundii, Veillonella parvula, Streptococcus sobrinus, Streptococcus sanguis, Streptococcus mutans, Streptococcus mitis* (*Streptococcus mitior*), *Lactobacillus casei, Lactobacillus acidophilus, Actinomyces viscosus*, and *Actinomyces neslundi* (*Actinomyces naeslundii*), which may cause infection and caries to tissues in the oral cavity, and thus protein attachment.

In addition, the present invention may bring about a fundamental therapeutic and preventive effect on teeth unlike when using GIC alone, by including the zwitterionic material together. That is, the present invention improves the bio activity by releasing more ions when the zwitterionic material is included together, and thus, improves the formation of tooth enamel, thereby improving the protective function and mechanical properties of the tooth itself against caries bacteria.

The effect according to the present invention is not limited by the contents exemplified above, and more various effects are included in the present specification.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention.

FIG. 2A shows the composition and content of dental glass ionomer cement compositions according to various examples below.

FIG. 2B shows a structural formula for a zwitterionic material used in one example of the present invention.

DETAILED DESCRIPTION

Advantages and features of the present invention and methods of achieving them will become apparent with reference to the examples described below in detail in conjunction with the accompanying drawings. However, the present invention is not limited to the examples disclosed below, but will be embodied in various different forms, and only these examples are provided only to complete the disclosure of the present invention and to fully inform a person with ordinary knowledge in the technical field to which the present invention pertains of the scope of the present invention, and the present invention is only defined by the scope of the claims.

The term "biofilm" as used herein may refer to a community consisting of proteins, fungi, bacteria, and the like formed on the surfaces of teeth and orthodontic devices. This biofilm may continue to grow and thicken due to constant temperature and humidity in the oral cavity and food residues that serve as nutrients for bacteria. The thickened biofilm produces toxic substances, causing dental caries and gum inflammation, which in turn causes gingivitis and periodontitis. Furthermore, when the biofilm is formed, proteins and the like from food residues are accumulated thereon to form plaque, and the plaque may thicken and harden to form tartar. Accordingly, in order to block the formation of plaque and tartar, it is necessary to inhibit the formation of biofilms that cause plaque and tartar.

The term "biomass" as used herein may refer to the total bacterial biomass of a community formed on a biofilm.

Hereinafter, with reference to FIG. 1, dental glass ionomer cement compositions used in various examples of the present invention and methods of preparing the same will be described.

Figure 1:
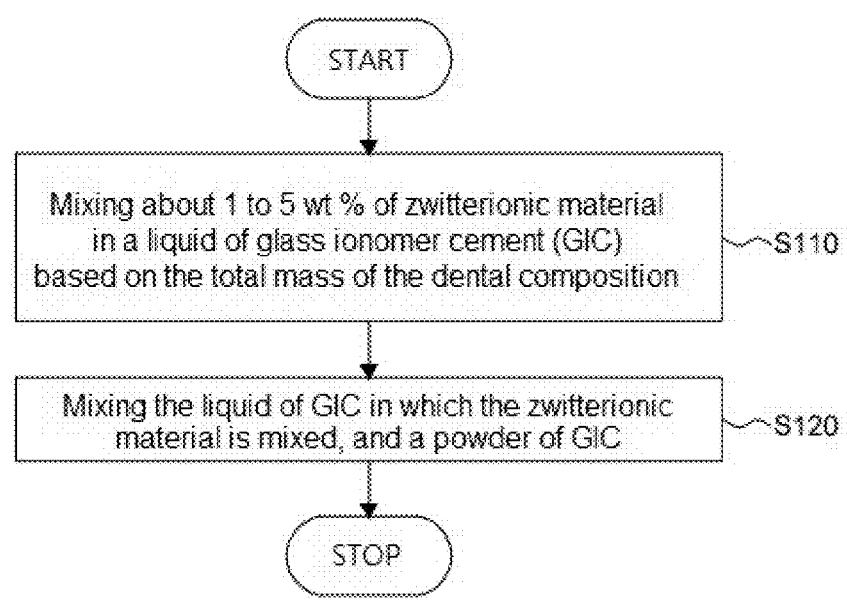
FIG. 1 exemplarily shows a dental glass ionomer cement composition according to one example of the present invention and a method of preparing the same.

FIG. 1 exemplarily shows a method of preparing a dental glass ionomer cement composition according to one example of the present invention.

The method of preparing a dental glass ionomer cement composition according to one example of the present invention may comprise the steps of: mixing about 1 to 5 wt % of zwitterionic material in a liquid of glass ionomer cement (GIC) based on the total mass of the dental glass ionomer cement composition (S110), and mixing the liquid of GIC in which the zwitterionic material is mixed, and a powder of GIC (S120).

In this case, the GIC used in various examples of the present invention may be formed by a reaction between mainly a fluoroaluminosilicate-based glass powder and a liquid containing a poly acid mainly composed of a polyacrylic acid, and the GIC used in various examples of the present invention may be, but is not limited to, Caredyne Restore (GC Corporation; Tokyo, Japan) commercially used in the are, and various GICs used in the same field of the present technology may be used.

For example, the GIC used in various examples of the present invention may comprise an acid-reactive inorganic filler powder and a liquid containing a poly acid. In this case, when an acid-reactive inorganic filler powder and a liquid containing a poly acid are mixed, carboxyl group ions (—COOH) released through an acid-base reaction may chemically bond with $Ca^{2+}$ in the tooth structure, so that it is possible to have high adhesion to the teeth.

In this case, the acid-reactive inorganic filler powder is an inorganic filler that chemically reacts in the presence of an acidic component, and may comprise one or more selected from the group consisting of, but not limited to, basic metal oxides, metal hydroxides, aluminosilicate glass, fluoroaluminosilicate glass, and calcium fluoroaluminosilicate glass, and all materials containing silica may be included.

However, preferred GICs used in various examples of the present invention may comprise calcium fluoroaluminosilicate glass, which may have particles of about 13 to 19 μm. Furthermore, the calcium fluoroaluminosilicate glass may be synthesized by one or more selected from the group consisting of, but not limited to, $SiO_2$, $Al_2O_3$, $CaF_2$, $Na_3AlF_6$, $AlF_3$, and $AlPO_4$.

Furthermore, the basic metal oxide of the GIC used in various examples of the present invention may include one or more selected from the group consisting of, but not limited to, barium oxide, strontium oxide, calcium oxide, magnesium oxide, and zinc oxide, and the metal hydroxide may include one or more selected from the group consisting of, but not limited to, calcium hydroxide, magnesium hydroxide, and strontium hydroxide.

In addition, the GIC used in various examples of the present invention may further include, but is not limited to barium glass to increase radiopacity.

In addition, the GIC used in various examples of the present invention may comprise a hydraulic powder containing silica glass, not the acid-reactive inorganic filler as described above. Accordingly, the GIC used in various examples of the present invention may be the aforementioned combination of a hydraulic powder and a liquid such as water.

On the one hand, the liquid of GIC used in various examples of the present invention may refer to a polymer having a plurality of acidic repeating units, wherein a functional group representing acidity may be attached to the backbone of each polymer, and may refer to a homopolymer or a copolymer.

In this case, since the liquid used in various examples of the present invention should contain an acidic repeating unit, it may comprise at least one selected from homopolymers and copolymers of acrylic acid, methacrylic acid, itaconic acid, maleic acid, glutaconic acid, aconitic acid, citraconic acid, mesaconic acid, fumaric acid or tiglic acid, and a copolymer of maleic acid and ethylene, but a preferred acidic copolymer may be polyacrylic acid. Accordingly, the liquid may be a liquid containing polyacrylic acid.

Furthermore, the liquid containing the poly acid used in various examples of the present invention may further include, but is not limited to, itaconic acid as an additive for improving physical properties, and may include all of a variety of materials for lowering the viscosity, that is, capable of preventing gelation by blocking intermolecular hydrogen bonding. In this case, when itaconic acid is used in the liquid used in various examples of the present invention, it may be used together with a polymer having a plurality of acidic repeating units, and the ratio thereof may be, but is not limited to, 1 itaconic acid for 2 polymers having a plurality of acidic repeating units.

In addition, the liquid used in various examples of the present invention may further include a complexing agent. For example, the complexing agent that may be contained in the liquid containing the poly acid, used in various examples of the present invention may further include one or more selected from the group consisting of, but not limited to, tartaric acid, citric acid, ethylene diamine tetraacetic acid (EDTA), salicylic acid, mellitic acid, dihydroxy tartaric acid, nitrilotriacetic acid (NTA), 2,4- and 2,6-dihydroxybenzoic acid, phosphono carboxylic acid, and phosphono succinic acid. In particular, the GIC in the dental glass ionomer cement composition according to one example of the present invention may comprise one or more ions selected from the group consisting of, but not limited to, Zn, Na, F, O, N, Ca, C, Cl, S, P, Si, and Al, and may comprise all of various ions capable of binding to and releasing the GIC.

First, the zwitterionic material used in the step of mixing the zwitterionic material in the liquid of GIC (S110) may comprise one or more selected from the group consisting of, but not limited to, 2-methacryloyloxyethyl phosphorylcholine (MPC), sulfobetaine methacrylate (SB), 1,2-dimyristoyl-sn-glycero-3-phosphatidylcholine (DMPC), 3-dimethylsulfoniopropanoate (DMSP), trigonelline, ectoine, betaine, N-(2-methacryloyloxy)ethyl-N,N-dimethylammonio propanesulfonate (SPE), N-(3-methacryloylimino) propyl-N, N-dimethylammonio propanesulfonate (SPP), carboxybetaine methacrylate (CBMA), and 3-(2'-vinyl-pyridinio)propanesulfonate (SPV), preferably MPC and/or SB, and more preferably MPC and SB.

More specifically, when MPC is used as the zwitterionic material in the step of mixing the zwitterionic material in the liquid of GIC (S110), the MPC may have, but is not limited to, a content of about 1 to 5 wt %, preferably about 2 to 4 wt %, and more preferably about 2.5 wt % to 3.5 wt %, based on the total mass of the dental glass ionomer cement composition according to one example of the present invention. In this case, when the MPC has a content of less than 1%, it may be an insufficient amount to exert the function of MPC, and thus the effect of GIC on mechanical properties, antibacterial properties and bioactivity may not be improved, and when the MPC has a content of exceeding 5%, the number of MPCs with strong attractive force increases, so that cohesion between them becomes strong due to the attractive force between them to cause aggregation of nanoparticles, which may cause small pores on the surface of the GIC. Furthermore, the pores generated in this way roughen the surface of the tooth treated with GIC, so that microorganisms may inhabit and adsorb to the tooth surface. In addition, when the MPC has a content of exceeding than 5%, since the physical properties of the main material such as GIC may be changed, the zwitterionic material used together with GIC may have a content of 1 to 5 wt %.

As described above, when the SB is included as a zwitterionic material in the dental glass ionomer cement composition according to one example of the present invention, the SB may have, but is not limited to, a content of about 1 to 5 wt %, and preferably about 2 to 4 wt %, based on the total mass of the dental glass ionomer cement composition according to one example of the present invention, and when added in excess or less than the above-mentioned content, the same problem as that of MPC may occur.

On the other hand, when the MPC and the SB are used simultaneously as zwitterionic materials, the total content of MPC and SB may be, but is not limited to, about 1 to 5 wt %, and preferably about 2 to 4 wt %, based on the total mass of the dental glass ionomer cement composition according to one example of the present invention.

Furthermore, in this case, the ratio of MPC and SB may be the same amount of 1 SB for 1 MPC based on the weight ratio. These GICs containing MPC and SB in a specific ratio have different partial charges of functional groups included in each material, and thus their net charge is not "zero" but has a charge in a specific direction, and polarity may occur. Accordingly, the dental glass ionomer cement composition according to one example of the present invention, which exhibits a higher polarity, may improve electrostatic interaction, that is, hydrogen bonding force to further increase the formation of a hydration layer. Accordingly, the ratio of MPC and SB may be, but is not limited to, about 1 MPC:about 1 SB based on the weight ratio, and the ratio of MPC to SB may be set between 1:3 to 3:1 based on the weight ratio.

On the other hand, the zwitterionic material used in the step of mixing the zwitterionic material in the liquid of GIC (S110) is a modifier capable of reinforcing the function without changing the physical properties of the GIC. More specifically, the zwitterionic material used in a method of preparing the dental glass ionomer cement composition according to one example of the present invention is a modifier capable of increasing the release of internal ions by blocking the bonds between bridging oxygens (BOs) present inside the GIC using a difference in the density of charges in the zwitterionic material to increase the ratio of non-bridging oxygens (NBOs). Accordingly, the modifier used in a method of preparing the dental glass ionomer cement composition according to one embodiment of the present invention may further comprise, in addition to the zwitterionic material described above, various materials capable of increasing the ratio of NBOs inside the GIC as it has a localized charge density.

For example, the modifier used in the method of preparing the dental glass ionomer cement composition according to one example of the present invention may comprise a material capable of strengthening the physical properties of the GIC, and may further comprise one or more selected from the group consisting of hydroxylapatite (HAp), glass fiber, silver-tin alloy, zirconia ($ZrO_2$), alumina ($Al_2O_3$), titania ($TiO_2$) nanoparticles, and bioactive glass.

Accordingly, the step of mixing the zwitterionic material in the liquid of GIC (S110) may comprise, together with the zwitterionic material, one or more selected from the group consisting of hydroxylapatite (HAp), glass fiber, silver-tin alloy, zirconia ($ZrO_2$), alumina ($Al_2O_3$), titania ($TiO_2$) nanoparticles, and bioactive glass.

In this case, the zwitterionic material and one or more materials selected from the group consisting of hydroxylapatite (HAp), glass fiber, silver-tin alloy, zirconia ($ZrO_2$), alumina ($Al_2O_3$), titania ($TiO_2$) nanoparticles and bioactive glass may not have a net charge of zero.

On the other hand, the method of preparing the dental glass ionomer cement composition according to one example of the present invention may further comprise a step of mixing one or more selected from the group consisting of a stabilizer, a flame retardant, an antistatic agent, a softener, a modifier, a filler, a fluorescence brightening agent, a lubricant, an inclusion reducing agent, a polycondensation catalyst, a defoamer, an emulsifier, a thickener, and a perfume, after the step of mixing the liquid of GIC in which the zwitterionic material is mixed, and a powder of GIC (S120).

Furthermore, the method of preparing the dental glass ionomer cement composition according to one example of the present invention may further comprise a step of mixing one or more selected from the group consisting of hydroxypropyl methylcellulose, hydroxyethyl cellulose, hydroxypropyl cellulose, polyvinyl alcohol, polyvinyl pyrrolidone, carbomer, and vinyl acetate resin, after the step of mixing the liquid of GIC in which the zwitterionic material is mixed, and a powder of GIC (S120).

That is, the dental glass ionomer cement composition according to one example of the present invention may further comprise the above-described material for use as a dental composition, i.e., a liner, a base, a cement, a restorative material, an adhesive, and the like, and may further comprise a variety of additives without being limited to the above-described materials. Accordingly, the dental glass ionomer cement composition according to one example of the present invention may be used for various purposes as a dental material for the dental composition.

Furthermore, the dental glass ionomer cement composition according to one example of the present invention may be used in various fields requiring an increase in ion release as well as the dental use as described in the dental composition. For example, the dental glass ionomer cement composition according to one example of the present invention may be used as a nanocarrier for delivering drugs and genes for the diagnosis and treatment of diseases using improved ion release properties, and may be used in various fields such as an agent for forming an organism requiring mineral synthesis, i.e., an osteoblast, as well as teeth.

After all, since the dental glass ionomer cement composition according to one example of the present invention formed by the preparation method as described above includes one or more zwitterionic materials, the release of ions is increased to increase the polarity, so that the anti-fouling activity to block the adsorption of proteins and bacteria may be increased. Furthermore, the in vivo mechanism chained by the increase in the release of ions as described above may improve the bioactivity and enamelization activity capable of killing various microorganisms including bacteria.

Hereinafter, with reference to FIGS. 2A to 5E, characteristics of a dental glass ionomer cement composition according to one example of the present invention will be described.

First, dental glass ionomer cement compositions according to various examples of the present invention to be described below may be a glass ionomer cement at least containing one or more zwitterionic materials. More specifically, with reference to FIG. 2A, an exemplary diagram for the composition and content of the dental glass ionomer cement compositions according to various examples below is shown.

Example 1 of the present invention contains 97 wt % of glass ionomer cement (GIC) and 3 wt % of 2-methacryloyloxyethyl phosphorylcholine (MPC) based on the entire dental composition, Example 2 of the present invention contains 97 wt % of GIC and 3 wt % of sulfobetaine methacrylate (SB) based on the total dental composition, and Example 3 of the present invention contains 97 wt % of GIC, 1.5 wt % MPC, and 1.5 wt % SB based on the total dental composition.

Furthermore, 100 wt % of glass ionomer cement (GIC) from Caredyne Restore (GC Corporation, Tokyo, Japan) was set as a control.

In this case, each of the examples and the control were prepared by mixing the zwitterionic material in powder form with a liquid of GIC, and then mixing them with a powder of GIC, according to the content preset in the preparation method as described above.

Furthermore, MPC and SB used in various examples of the present invention are zwitterionic materials (zwitterions) including an anionic group and a cationic group at the same time. More specifically, with reference to FIG. 2B, a structural formula for a zwitterionic material used in one example of the present invention is shown.

2-Methacryloyloxyethyl phosphorylcholine (MPC) is attracting attention as a bio-friendly and eco-friendly material that mimics the hydrophilic functional group of phosphatidylcholine (PC), which is a component of the biological double membrane phospholipid. In addition, since MPC includes the above-described hydrophilic functional group, it may form a stable hydration shell with high hydrophilicity, thereby having excellent anti-fouling function.

Furthermore, since sulfobetaine methacrylate (SB) includes sulfobetaine having a sulfonate functional group instead of the above-described phosphate group of phosphatidylcholine, it is bio-friendly and has high potential for in vivo application, similar to MPC, and is a zwitterion having both a sulfonate anion group and an ammonium cation group in one molecule. Moreover, SB also has an antifouling function and may be easily and conveniently synthesized compared to PC-based polymers, and thus may be easily used for more commercial applications.

After all, although the above-described zwitterionic materials MPC and SB may show some degree of difference, most dipolar polymers may inhibit non-specific adsorption in aqueous solution through hydrophobic or electrostatic attraction. In addition, the addition of a zwitterionic material as an additive may inhibit suppress thermal and chemical denaturation of the protein. In particular, the above-described MPC and SB may be used more stably in vivo by mimicking in vivo components.

Figure 3:
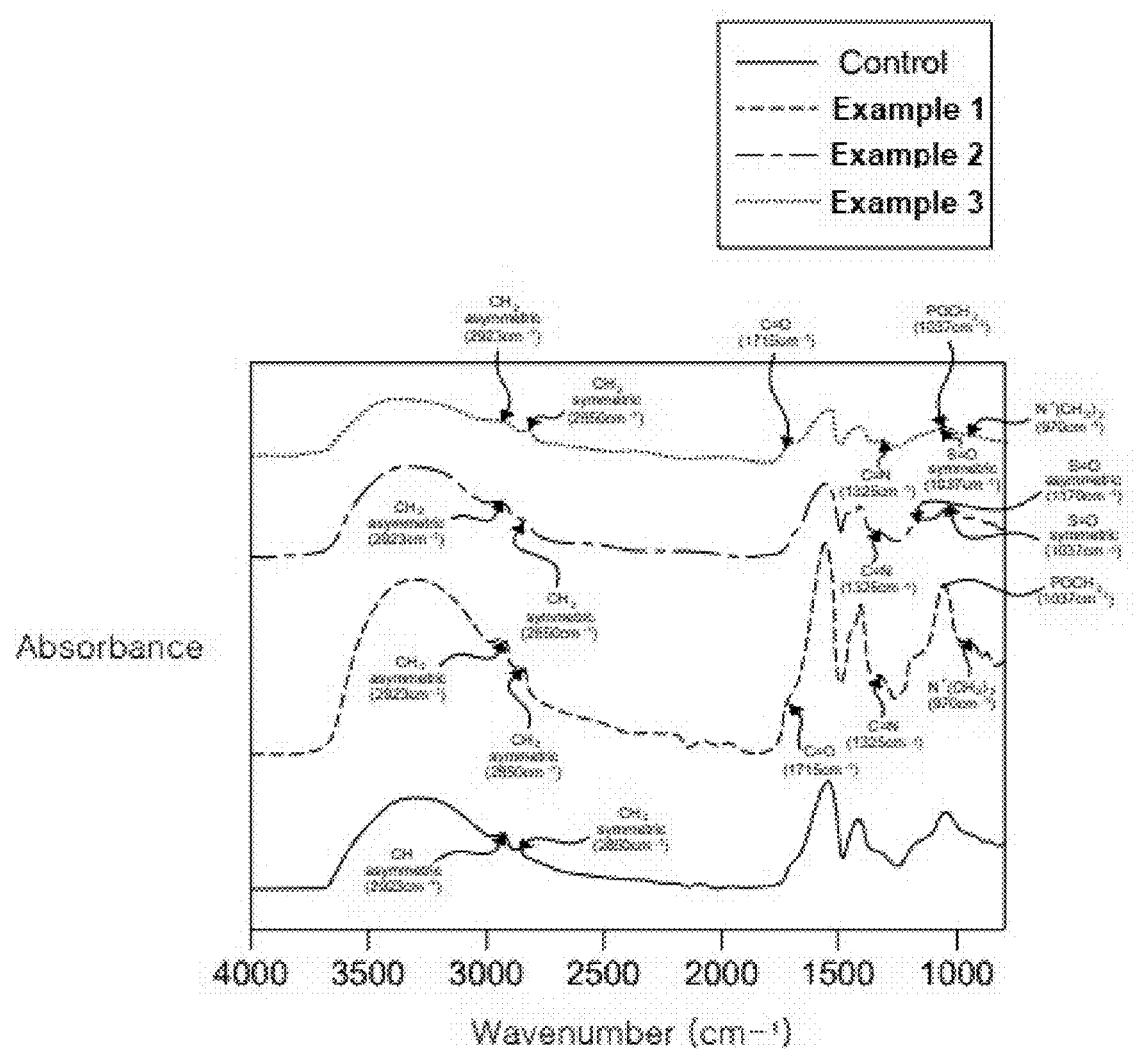
FIG. 3 shows the results for Fourier transformed infrared spectroscopy (FTIR) of the examples of the present invention and the control.

With reference to FIG. 3, the results for Fourier transformed infrared spectroscopy (FTIR) of the examples of the present invention and the control are shown. In this case, FTIR was performed to confirm the composition of the examples of the present invention synthesized according to the above-described composition, and a disk specimen having a diameter of 15 mm and a thickness of 2 mm was prepared and used for analysis. Furthermore, results were obtained from spectra (4000 to 800 $cm^{-1}$) with a resolution of 4 $cm^{-1}$ using instrument's OMNIC spectra software.

Examples 1 to 3 showed a peak corresponding to C=O at 1715 $cm^{-1}$ and a peak corresponding to C—N at 1325 $cm^{-1}$ in common, but the control did not show the above-mentioned peaks.

Furthermore, Examples 1 to 3 showed a peak corresponding to $N^+(CH_3)_3$ at 970 $cm^{-1}$ and a peak corresponding to POCH at 1060 $cm^{-1}$ in common, along with the above-mentioned peaks, but the control did not show the above-mentioned peaks.

Furthermore, Examples 2 and 3 showed a peak corresponding to S=O symmetric at 1037 $cm^{-1}$ and a peak corresponding to S=O asymmetric at 1170 $cm^{-1}$ in common, but the control did not show the above-mentioned peaks.

That is, Examples 1 to 3 of the present invention show each characteristic peak depending on the functional group contained in the zwitterionic material added to each, which may mean that each of the zwitterionic materials is stably bound to the GIC.

Figure 4A:
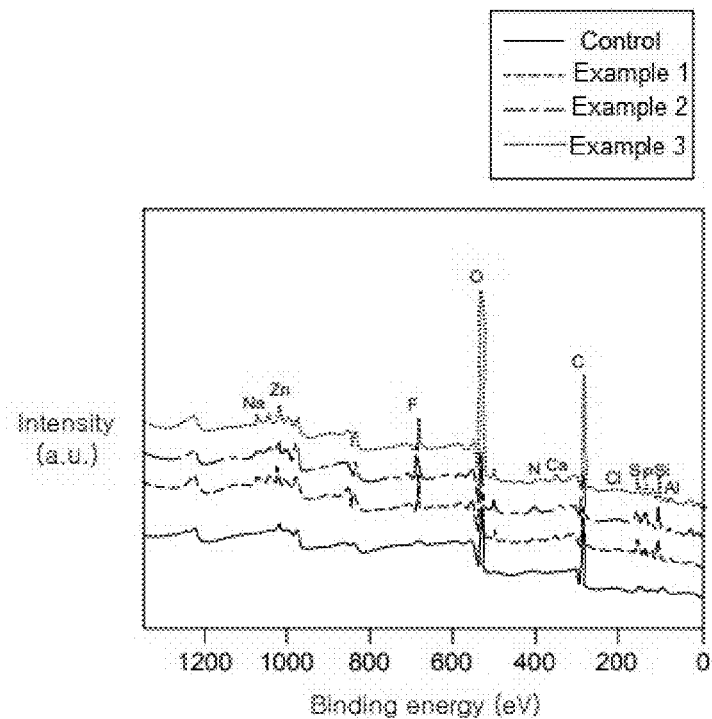
FIG. 4A shows the results for X-ray photoelectron spectroscopy (XPS).

Furthermore, with reference to FIG. 4A, the results for X-ray photoelectron spectroscopy (XPS) are shown. In this case, XPS, which is an experimental method for ion release analysis, was analyzed after preparing the examples of the present invention and the control with specimens of 10×2 mm size and storing them at 37° C. for 24 hours.

The atomic composition of the surface of the material of Examples 1 to 3 of the present invention includes zinc (Zn) as in the control, and is shown to include Na, F, O, N, Ca, C, Cl, S, P, Si, and Al in common. That is, the composition for the GIC of Examples 1 to 3 of the present invention was found to be the same as that of the control, which may mean that Examples 1 to 3 of the present invention does not change the bonding state and the composition state of atoms due to the addition of the zwitterionic material and maintains the characteristics of the present GIC.

Figure 4B:
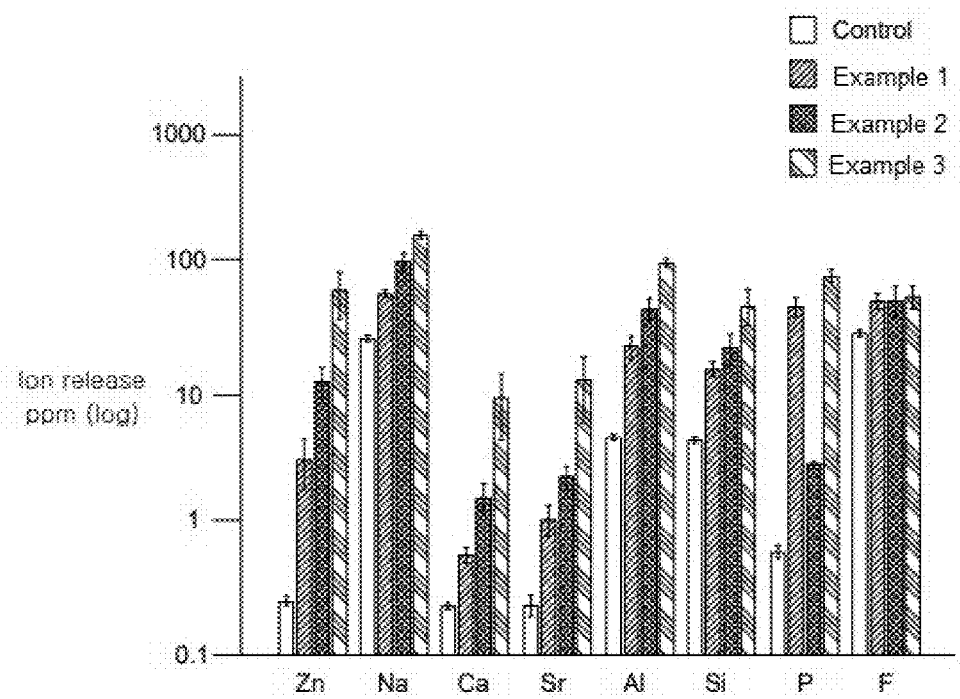
FIG. 4B shows the results for the profile of ions released from the examples of the present invention.

Furthermore, with reference to FIG. 4B, the results for the profile of ions released from examples of the present invention are shown.

More specifically, Example 3 of the present invention including MPC and SB is shown to release the most significantly all kinds of ions (p<0.001).

In particular, in the case of Zn, the released amount of the control is about 0.24 ppm, and the released amounts of Examples 1 to 3 are about 3.19 ppm, about 12.40 ppm, and about 61.98 ppm, respectively, which is shown that the released amount of Zn in the examples of the present invention including the zwitterionic material is about 13 to 260 times higher than that of the control including no zwitterionic material.

In addition, in the case of Ca, the released amount of the control is about 0.23 ppm, and the released amounts of Examples 1 to 3 are about 0.58 ppm, about 1.58 ppm, and about 9.25 ppm, respectively, which is shown that the released amount of Ca in the examples of the present invention including the zwitterionic material is about 2 to 40 times higher than that of the control including no zwitterionic material.

In addition, in the case of Sr, the released amount of the control is about 0.23 ppm, and the released amounts of Examples 1 to 3 are about 1.08 ppm, about 2.27 ppm, and about 12.68 ppm, respectively, which is shown that the released amount of Sr in the examples of the present invention including the zwitterionic material is about 5 to 55 times higher than that of the control including no zwitterionic material.

In addition, in the case of P, the released amount of the control is about 0.61 ppm, and the released amounts of Examples 1 to 3 are about 46.58 ppm, about 2.90 ppm, and about 81.13 ppm, respectively, which is shown that the released amount of P in the examples of the present invention including the zwitterionic material is about 5 to 133 times higher than that of the control including no zwitterionic material.

That is, since the dental glass ionomer cement composition according to one example of the present invention includes a zwitterionic material, the released amount of ions may be increased. In particular, it was shown that ion release may be most effectively improved in Example 3 including both MPC and SB, which may mean that the effect of GIC on ion release may be further improved when two or more kinds of zwitterionic materials are combined in a specific ratio rather than when used alone.

Figure 4C:
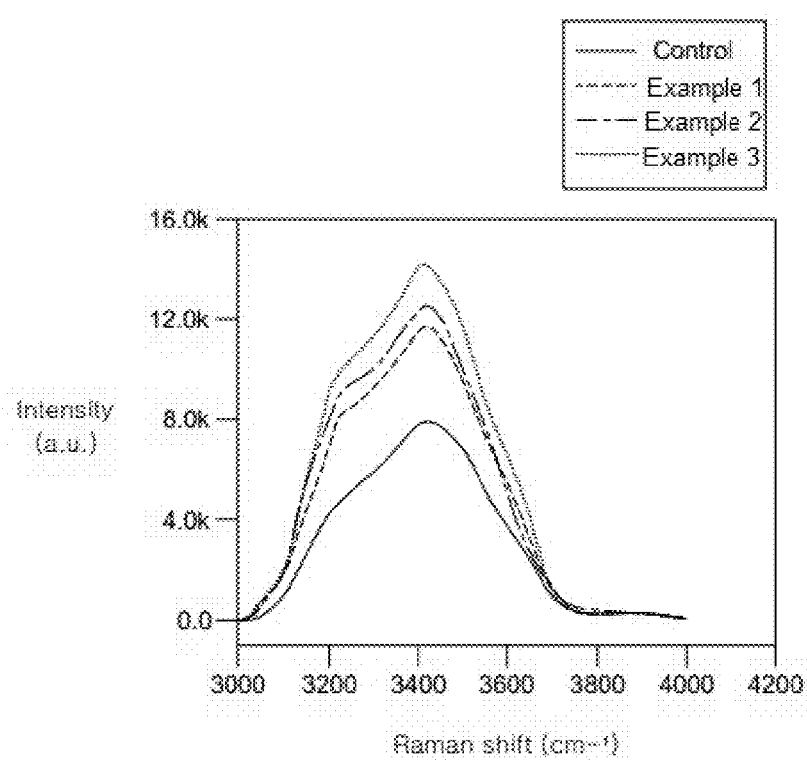
FIG. 4C shows the Raman spectrum result that is a result of a vibration frequency caused by ions released from a dental glass ionomer cement according to one example of the present invention.

Accordingly, with reference to FIG. 4C, the Raman spectrum results, which are the results of the vibration frequency due to the ions described above, are shown, which is shown that since Examples 1 to 3 of the present invention increase the released amount of ions on the surface of the composition by the zwitterionic material as described above, the intensity of vibrational energy therefor is higher than that of the control. In addition, similar to the result of FIG. 4B, Example 3 of the present invention showed the highest intensity of vibrational energy due to ion release, which may mean that the combination of MPC and SB in a specific ratio may further improve the effect of GIC on ion release.

The improved ion release effect further increased by the combination of MPC and SB may be caused by increased polarity since the amount of intrinsic charge appearing in the functional groups of each material is different.

Figure 5A:
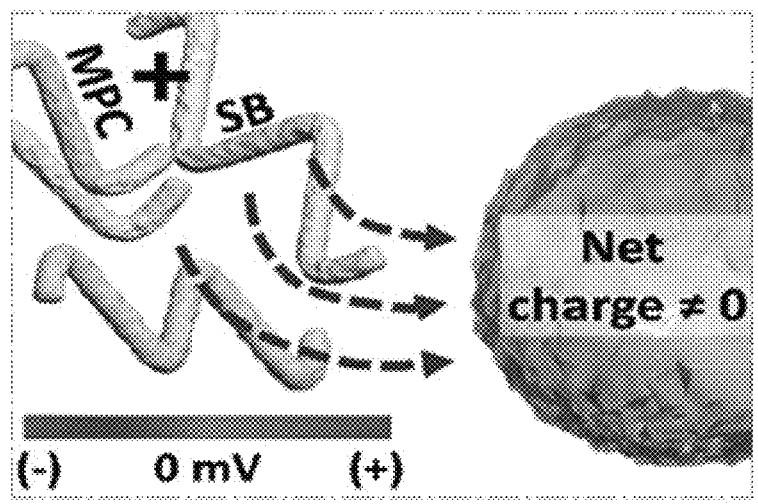
FIG. 5A shows an exemplary diagram for the net charge of a zwitterionic material.
Figure 5A:
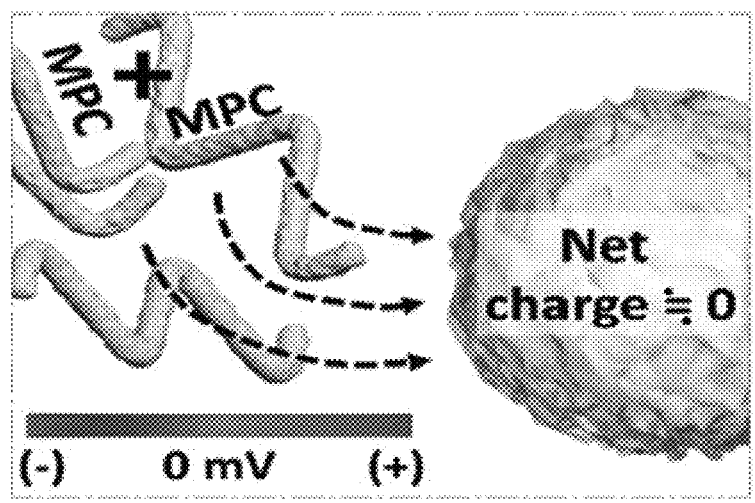

For example, with reference to FIG. 5A, an exemplary diagram for the net charge of a zwitterionic material is shown. First, with reference to (a) of FIG. 5A, the magnitudes of positive and negative charges included in each of MPC and SB are different from each other since the functional groups included in each are different. Accordingly, when MPC and SB are included together, the net charge does not converge to "zero," and strong polarity may occur. Thus, the remarkably improved ion release effect according to the combination of MPC and SB described above in FIGS. 4A to 4B may be caused by the occurrence of such strong polarity.

On the other hand, with reference to (b) of FIG. 5A, when MPC or SB are each alone, the sum of all charges (net charge) may converge close to "zero" since the zwitterionic material included is the same material, and thus, the polarity may be weaker than the above-described combination of two or more.

However, zwitterionic materials such as MPC or SB, i.e., modifiers, may also exhibit polarity when included in the GIC alone, and thus, the improved ion release effect of GIC may be caused as in Examples 1 and/or 2 of FIGS. 4A and 4B.

Figure 5B:
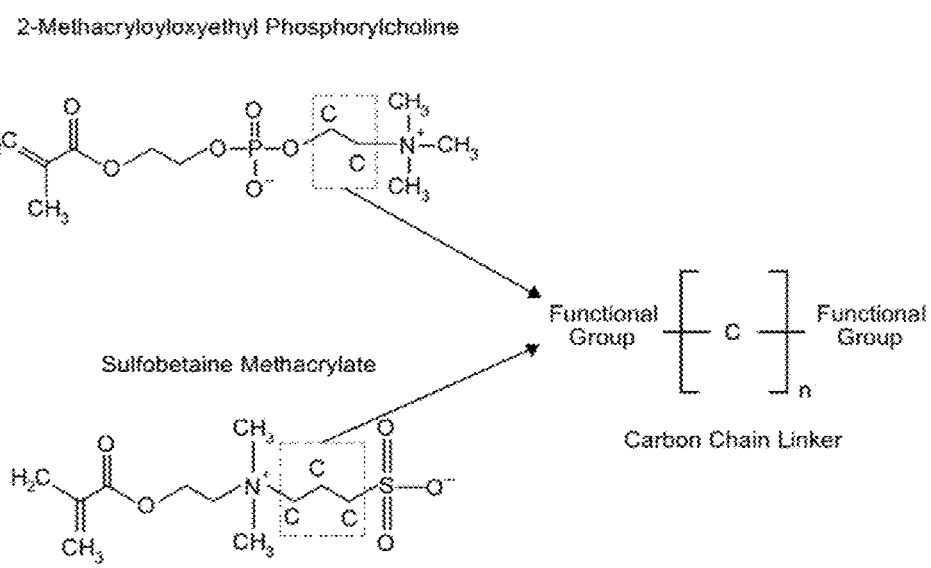
FIG. 5B shows an exemplary diagram for the carbon chain of a zwitterionic material.

More specifically, with reference to FIG. 5B, an exemplary diagram for the carbon chain of a zwitterionic material is shown. As a modifier used in one example of the present invention, a zwitterionic material is included, and the zwitterionic material has positive and negatively charged functional groups connected through a carbon chain, that is, a carbon-carbon bond.

As the length of the carbon chain included in such zwitterionic material increases, the magnitude of the dipole moment, that is, the polarization for each functional group increases, so that the net charge does not converge to "zero" and the polarity may occur. Accordingly, even when the modifier including the zwitterionic material of the present invention includes one zwitterionic material, and in particular, when the net charge does not become zero due to a combination of two or more zwitterionic materials, it may have the remarkably improved ion release effect compared to the GIC including no zwitterionic material. After all, the modifier that may be included in the dental glass ionomer cement composition according to one example of the present invention may include not only the above-described zwitterionic material, but also various materials that do not converge to "zero" in net charge and have a polarity.

Figure 5C:
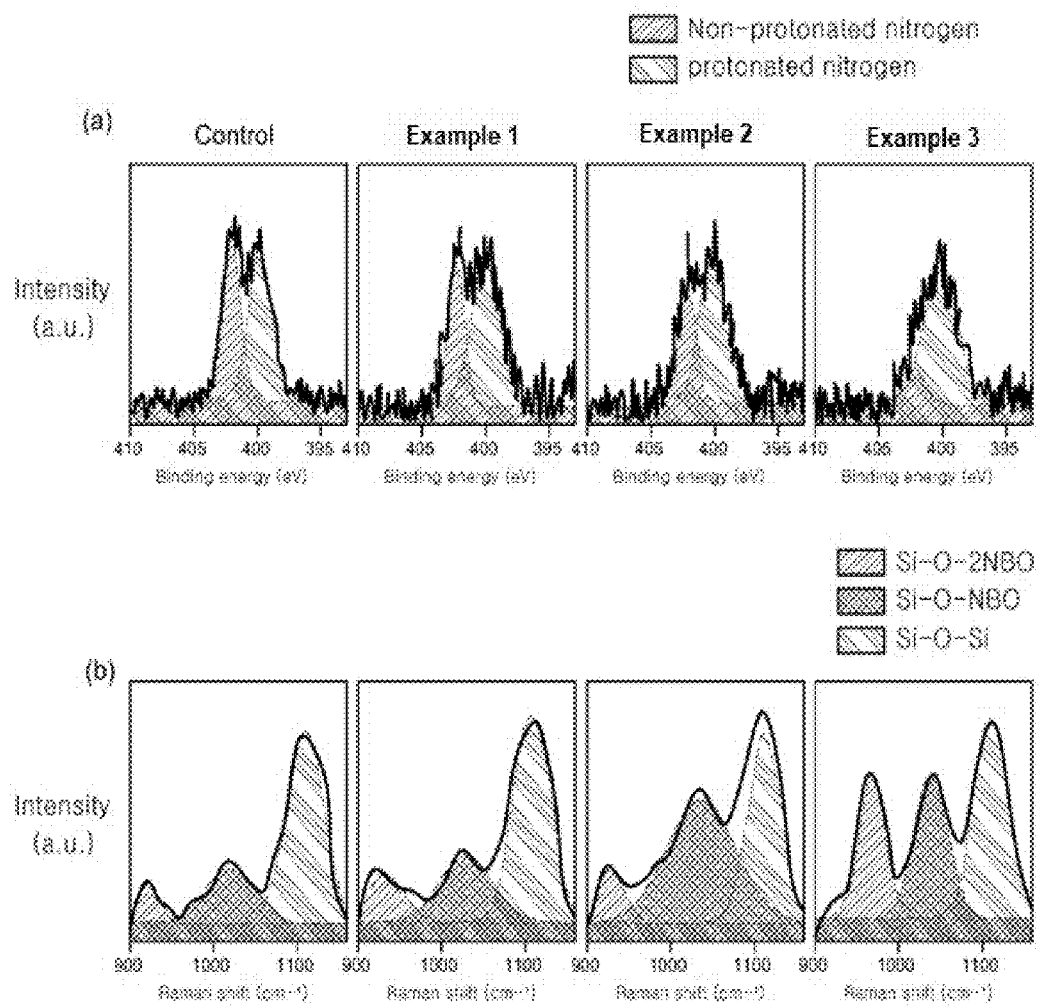
FIG. 5C shows XPS and Raman spectrum results for the net charge in one example of the present invention due to a zwitterionic material.

Furthermore, with reference to FIG. 5C, XPS and Raman spectrum results for the net charge in one example of the present invention due to a zwitterionic material are shown. First, with reference to (a) of FIG. 5C, when a zwitterionic material is included, the ratio of protonated nitrogen is shown to increase, and in particular, Example 3 including MPC and SB together is shown to have a high strength of protonated nitrogen, which may mean that the cation may increase due to the addition of protonated nitrogen, that is, a zwitterionic material. Furthermore, since nitrogen generates a repulsive force between molecules as it becomes protonated, intermolecular aggregation is minimized and strong polarity occurs, and thus, ion release may increase.

Moreover, with reference to (b) of FIG. 5C, the proportion of non-bridging oxygen (NBO) and bridging oxygen (BO) cross-linked with Si appears differently depending on the added zwitterionic material, and Example 2 appears to have a high proportion of NBO. That is, when two or more different zwitterionic materials are included, since the proportion of Si—O—NBO and Si—O-2NBO having a relatively unstable structure is higher than that of Si—O—Si having atomic structural stability, the difference in charge density due to them, that is, ionicity (polarity) may increase.

Figure 5D:
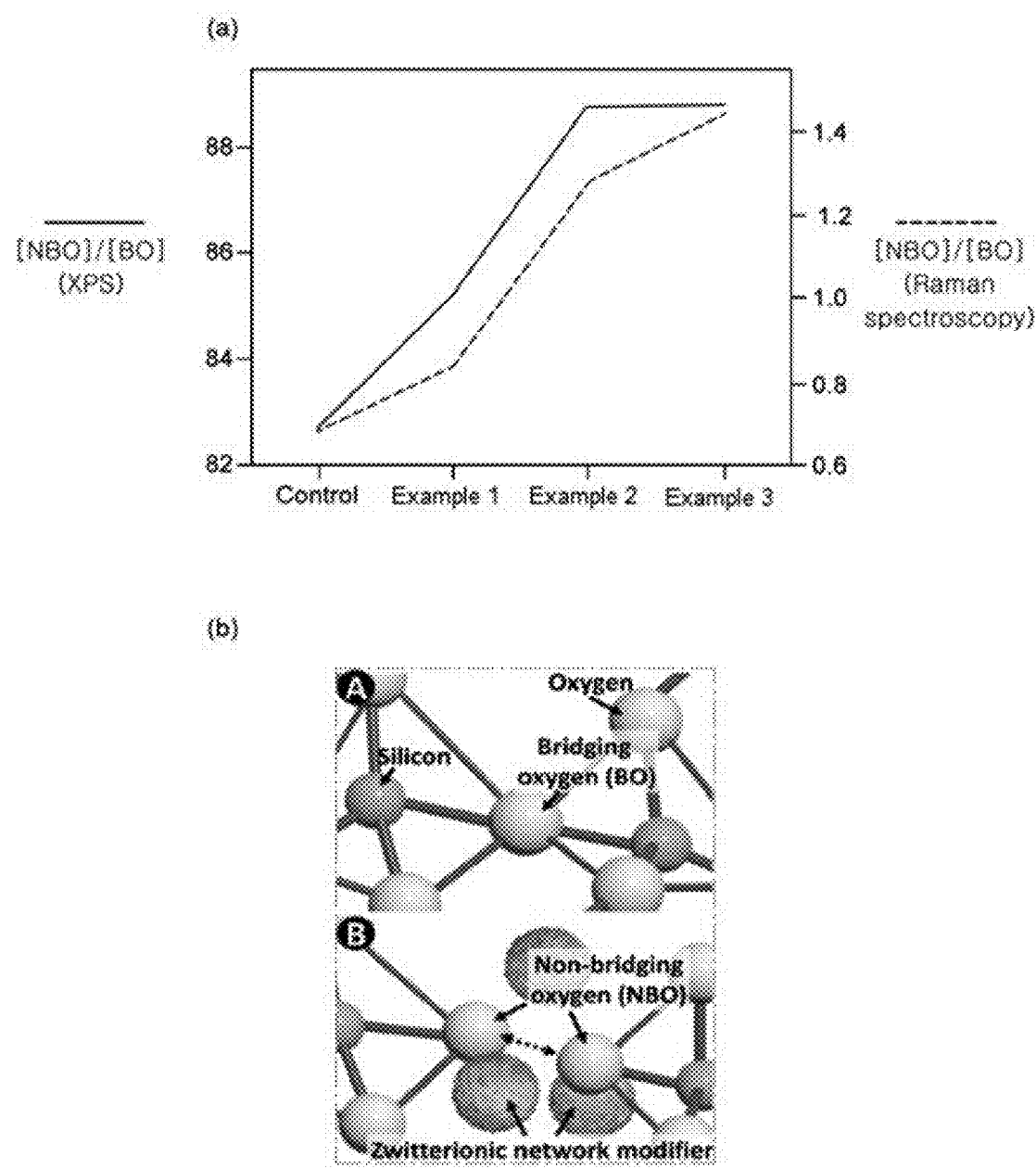
FIG. 5D shows a graph quantifying the results of FIGS. 5A and 5C described above.

More specifically, with reference to FIG. 5D, graphs for the results of FIGS. 5A and 5C described above are shown, and when only a single zwitterionic material (zwitterionic network modifier) is included, the net charge converges to zero. In contrast, when two or more kinds of zwitterionic materials (zwitterionic network modifiers) are included, the net charge may be determined by the partial charge distribution, and since the partial charge of the MPC (–) functional group is –1.5952 and the partial charge of the SB (–) functional group is –0.9537, the partial charge becomes heterogeneous, so that the bond of the cross-linked oxygen may be more effectively broken.

After all, since the dental glass ionomer cement composition according to one example of the present invention includes a zwitterionic material, the bonding of Si—O—Si is broken due to strong attractive force by the (–) functional group of the zwitterionic material, so that ion release increases (forming ion release channels), and thus, the polarity may increase. In particular, when two or more kinds of zwitterionic materials are included, since the difference in charge therebetween becomes larger, more ions may be released by their different charges.

Furthermore, as the polarity increases due to the zwitterionic material, the dental glass ionomer cement composition according to one example of the present invention may form strong hydrogen bonding, and thus, may from a thicker hydration layer.

Figure 5E:
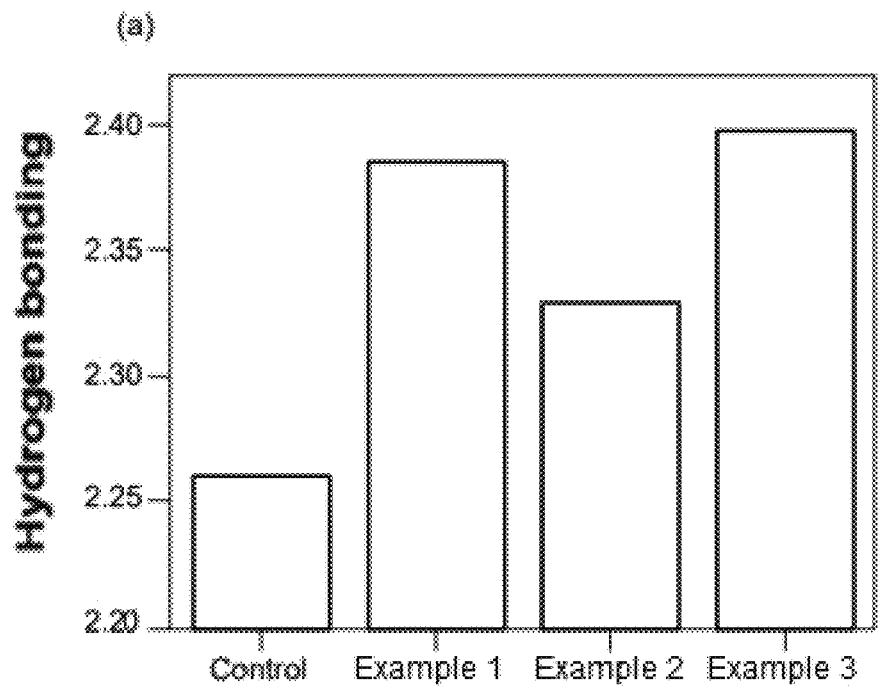
FIG. 5E shows the results for hydrogen bonding of the examples of the present invention and the control.
Figure 5E:
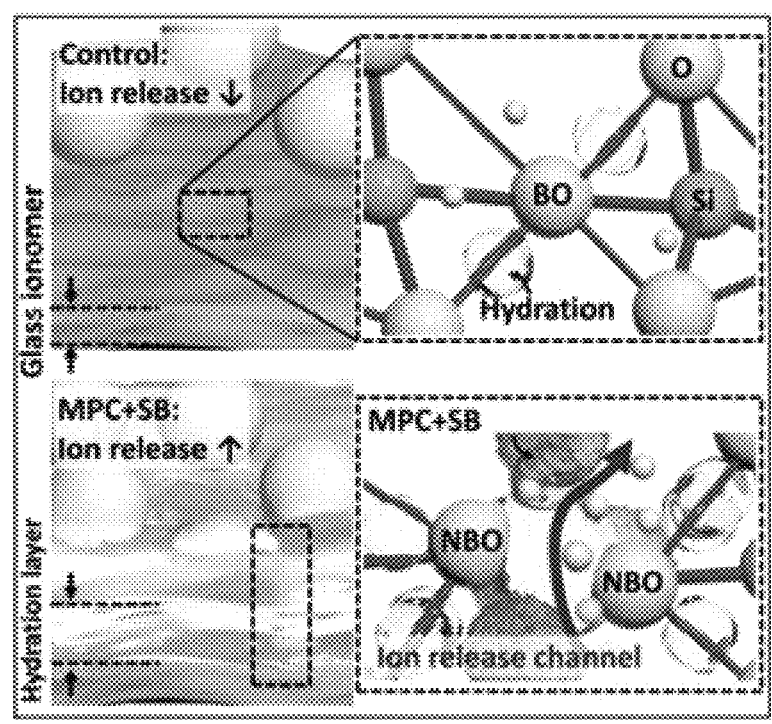

Accordingly, with reference to FIG. 5E, Examples 1 to 3 of the present invention are shown to have stronger hydrogen bonding strength than the control. Furthermore, Example 3 of the present invention, which includes two or more kinds of zwitterionic materials among the examples of the present invention is shown to release more ions by partial charge of the functional groups of each zwitterionic material, as described above, and thus have the strongest hydrogen bonding strength.

After all, since the dental glass ionomer cement composition according to one example of the present invention includes a zwitterionic material, ion release may be improved, and thus, hydrogen bonding strength may be improved to form a thicker hydration layer. Furthermore, the hydration layer formed by the above-described characteristics may improve the antifouling effect capable of blocking the adsorption of substances harmful to teeth, such as biofilm, to the dental glass ionomer cement composition according to one example of the present invention.

Hereinafter, with reference to FIG. 6A and FIG. 6B, the antifouling effect of a dental glass ionomer cement composition according to one example of the present invention will be described.

Figure 6A:
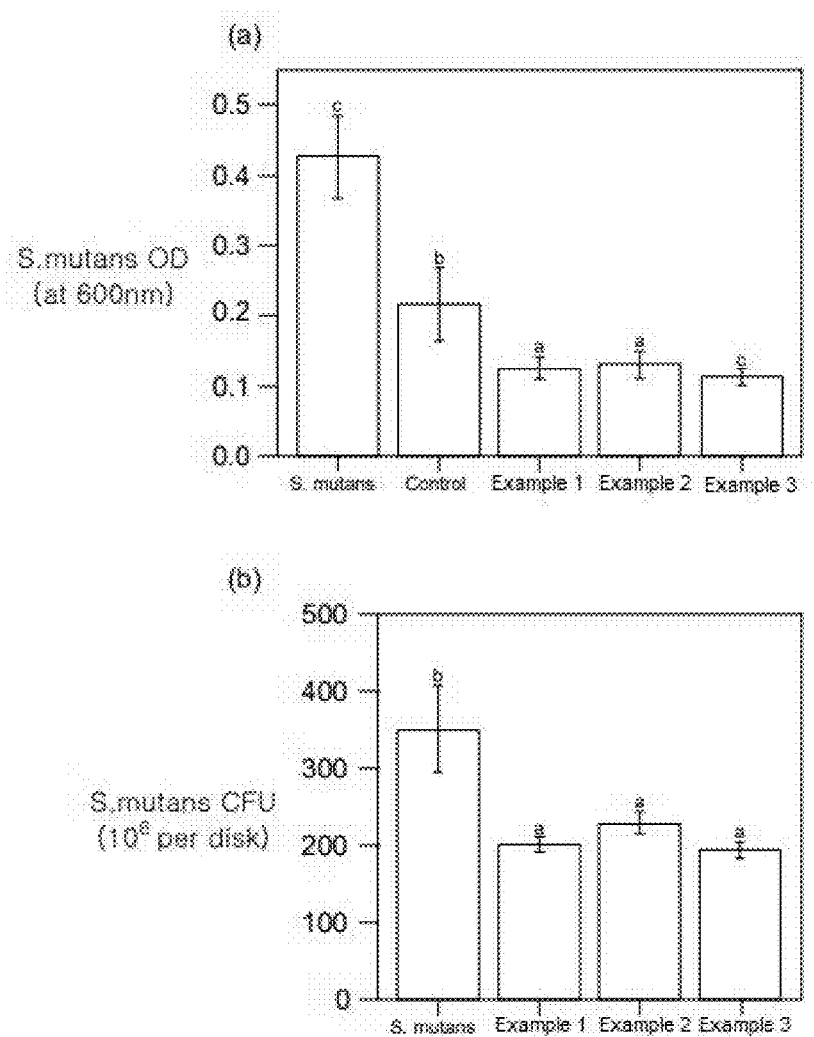
FIG. 6A shows the results for the antibacterial effect of a dental glass ionomer cement composition according to one example of the present invention.

First, with reference to FIG. 6A, the results for the antibacterial effect of a dental glass ionomer cement composition according to one example of the present invention are shown. In this case, the control and Examples 1 to 3 of the present invention were prepared in the form of a disk-shaped specimen by a mold having a diameter of 5 mm and a thickness of 1.5 mm, and a BHI medium containing dental caries bacteria (*Streptococcus mutans*) was placed on the specimen and cultured at 37° C. for 18 hours, and then the specimen and bacteria were separated through ultrasonication, and the OD value was measured at 600 nm for the separated bacteria using a microplate reader (Epoch, BioTek Instruments; VT, USA), and then the OD value was evaluated for this. Furthermore, in order to evaluate the antibacterial properties by self-release of ions for the control, a specimen including no GIC was prepared and comparatively evaluated.

Accordingly, with reference to (a) of FIG. 6A, as the ions are released as described in FIGS. 4A and 4B above, the control is shown that antibacterial action occurs. However, it is shown that the number of surviving dental caries bacteria present in the specimen is greater than that of Examples 1 to 3 of the present invention. That is, Examples 1 to 3 of the present invention showed a significantly lower number of dental caries bacteria than the control, which may mean that they had more improved antibacterial activity ($p<0.01$). In particular, Example 3 of the present invention was shown to have significantly the lowest number of dental caries bacteria, which may mean that two or more kinds of zwitterionic substances may most effectively provide antibacterial activity.

Next, with reference to (b) of FIG. 6A, the colony forming unit (CFU) results of the dental caries present in each of examples and the control are shown. The CFU level of dental caries attached to Examples 1 to 3 of the present invention is shown to be significantly lower compared to that of the control (p<0.01), and it is shown that there is no difference between Examples 1 to 3. These results may mean that as the zwitterionic material blocks the adsorption of dental caries, the number of obtained dental caries is reduced.

Figure 6B:
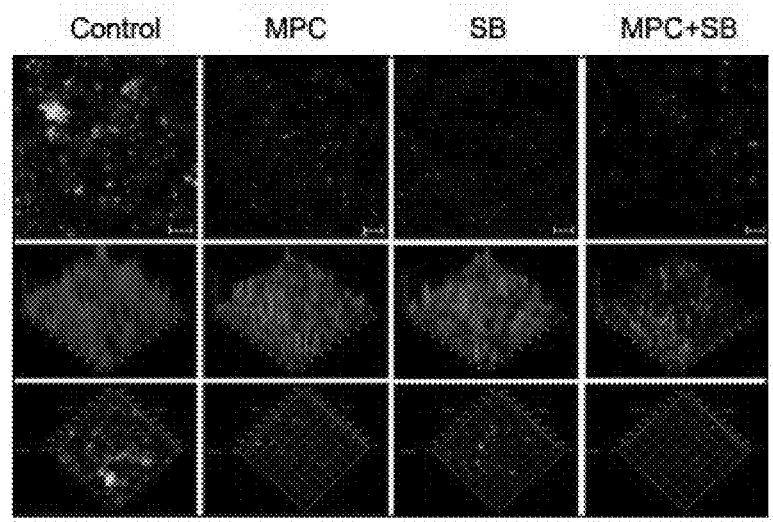
FIG. 6B shows the results for the biofilm prevention effect of a dental glass ionomer cement composition according to one example of the present invention.
Figure 6B:
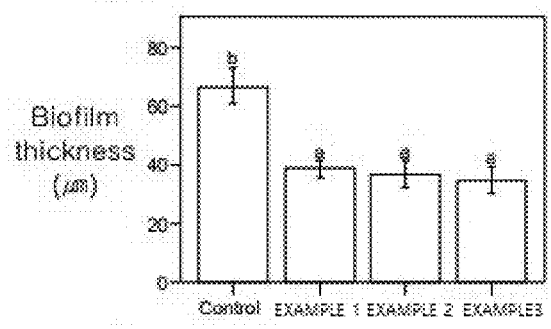
Figure 6B:
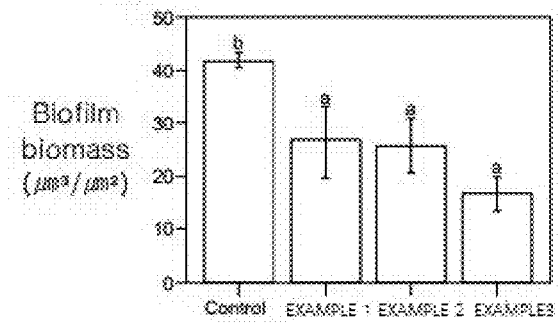

Furthermore, with reference to FIG. 6B, the results for the biofilm prevention effect of a dental glass ionomer cement composition according to one example of the present invention are shown. In this case, as a biofilm model, saliva was collected from 6 donors who did not have dental caries or periodontal disease, did not take antibiotics for 3 months, did not brush their teeth for 24 hours before collection, and did not eat for 2 hours before collection, and mixed in the same ratio. The mixed saliva was then mixed in a proportion of 1 for 50 McBain broth medium, and used as a biofilm model. Furthermore, the control and Examples 1 to 3 of the present invention were prepared in the form of a disk-shaped specimen by a mold having a diameter of 5 mm and a thickness of 1.5 mm, and the biofilm model was placed on the specimen and cultured for 24 hours in a $CO_2$ incubator at 37° C. while changing the medium at intervals of 8 and 16 hours. The specimen on which the biofilm was formed was then stained using a live/dead bacterial viability kit (Molecular Probes; Eugene, OR, USA) that may check whether microorganisms are live or dead, and biofilms were visualized at 5 randomly selected locations using a confocal laser microscope (laser scanning microscopy, CLSM, LSM880, Carl Zeiss; Thornwood, NY, USA). An image of the biofilm laminated in the axial direction was then acquired, the thickness of each biofilm was measured using Zen (Zen, Carl Zeiss; Thornwood, NY, USA), and biomass was analyzed using ImageJ (NIH, Bethesda, MA, USA).

First, with reference to (a) of FIG. 6B, the control is shown that green fluorescence for living microorganisms is most expressed. Furthermore, it is shown that the laminated biofilm is also the thickest. (Scale bar indicates 100 μm)

In contrast, Examples 1 to 3 of the present invention show that low green fluorescence is expressed less than the control, and in particular, Example 3 shows that red fluorescence indicating dead microorganisms is expressed the most.

Accordingly, with reference to (b) of FIG. 6B in which the thickness of the biofilm is quantified among the results of (a) of FIG. 6B above, Examples 1 to 3 of the present invention show that the thickness of the biofilm is significantly lower than that of the control (p<0.001), and it is shown that the thickness of the biofilm grown in the examples of the present invention is 0.5 to 0.6 times lower than that of the control.

Furthermore, with reference to (c) of FIG. 6B in which the thickness of the biomass is quantified among the results of (a) of FIG. 6B above, Examples 1 to 3 of the present invention show that the biomass of the biofilm is significantly lower than that of the control (p<0.001), and it is shown that the biomass of the biofilm grown in the examples of the present invention is 0.38 to 0.6 times lower than that of the control.

From the above results, as the dental glass ionomer cement composition according to one example of the present invention includes a zwitterionic material, the formation of a hydration layer is improved, so that adhesion to proteins and microorganisms is reduced, and thus, the formation of a biofilm may be inhibited.

Furthermore, the dental glass ionomer cement composition according to one example of the present invention shows that due to the release of ions by the zwitterionic material in addition to the prevention of adhesion by the formation of the hydration layer described above, that is, the antifouling effect, the biocidal effect of microorganisms is improved. That is, the present invention may mean to have an antibacterial effect on microorganisms in addition to the antifouling effect.

On the other hand, by including a zwitterionic material, the dental glass ionomer cement composition according to one example of the present invention improves ion release and also improves release of P and Ca among them, and thus is involved in cell adhesion and proliferation. More specifically, when calcium hydroxide is continuously generated by the release of P and Ca, the pH in the oral cavity increases, and thus, an antibacterial environment may be created, thereby, as a series of signal systems, immune cells such as cytokines may be produced. Furthermore, the produced immune cells induce cells forming hard tissue, and the induced cells form apatite and hydroxy apatite on the tooth surface, so that bone activation ability may be improved.

Figure 7A:
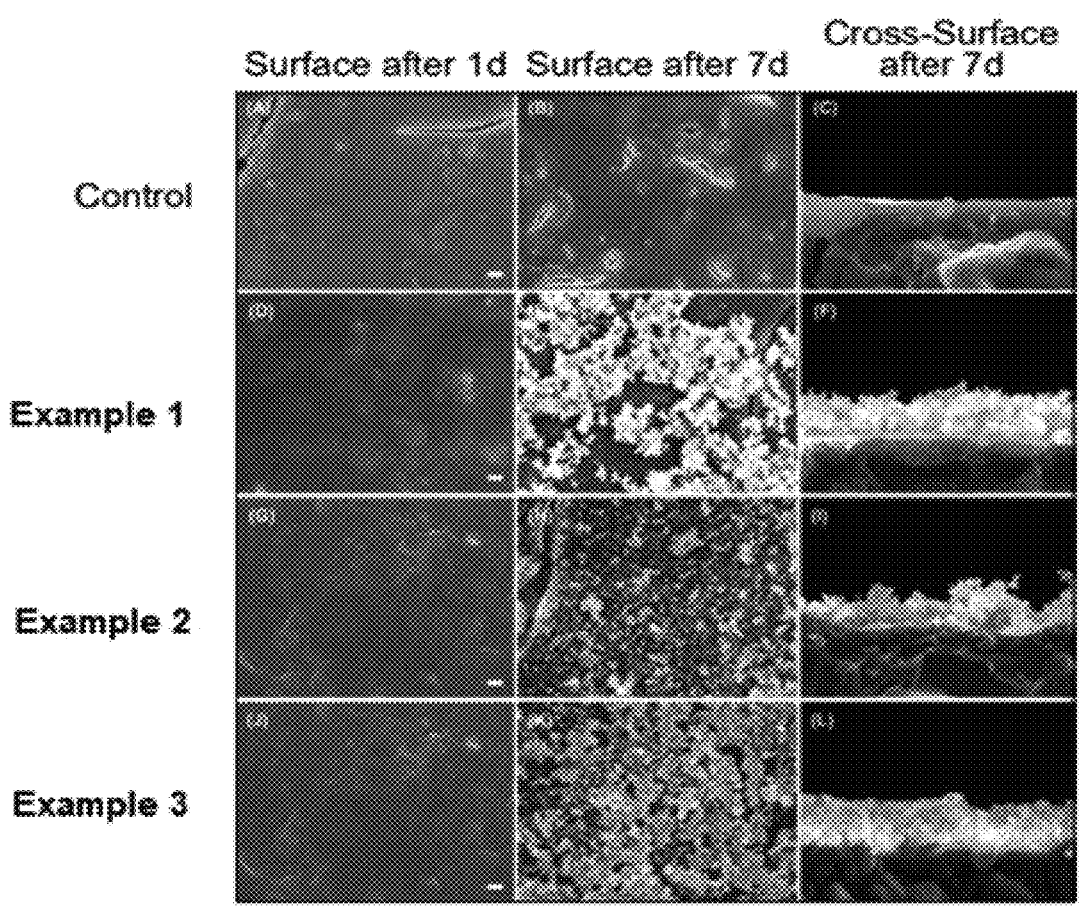
FIG. 7A shows an SEM image of a surface and a cross-section of a dental glass ionomer cement composition according to one example of the present invention.

Accordingly, with reference to FIG. 7A, an SEM image of a surface and a cross-section of a dental glass ionomer cement composition according to one example of the present invention is shown. In this case, in order to evaluate the apatite forming ability of the dental glass ionomer cement composition according to on example of the present invention, it was prepared in the form of a disk-shaped specimen by a mold having a diameter of 5 mm and a thickness of 1.5 mm, and the above-mentioned specimen was immersed in simulated body fluid (SBF) similar to the blood component for 7 days, and then the layer formed on the specimen was analyzed using a field-emission scanning electron microscope and image J software.

More specifically, the control group shows that apatite containing Ca and P, that is, apatite is hardly formed. That is, the control group has very low or no bioactivity capable of mineralizing the surface of GIC, which may mean that apatite is not formed.

In contrast, Examples 1 to 3 of the present invention show that apatite is thicker and more formed than in the control, and in particular, Example 3 shows that the thickest and finest apatite is formed.

Figure 7B:
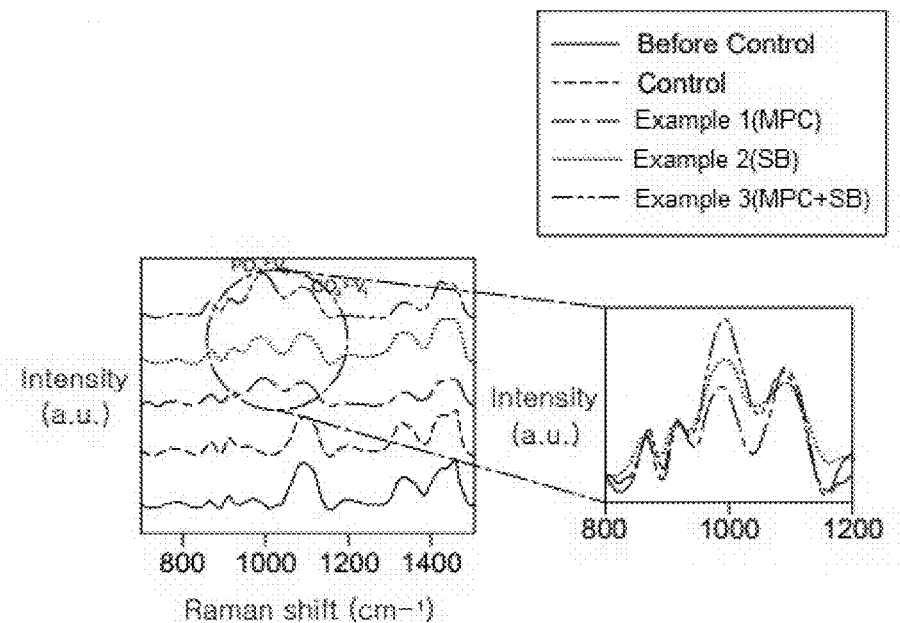
FIG. 7B shows the Raman spectrum result for the bone activation ability in one example of the present invention due to a zwitterionic material.
Figure 7B:
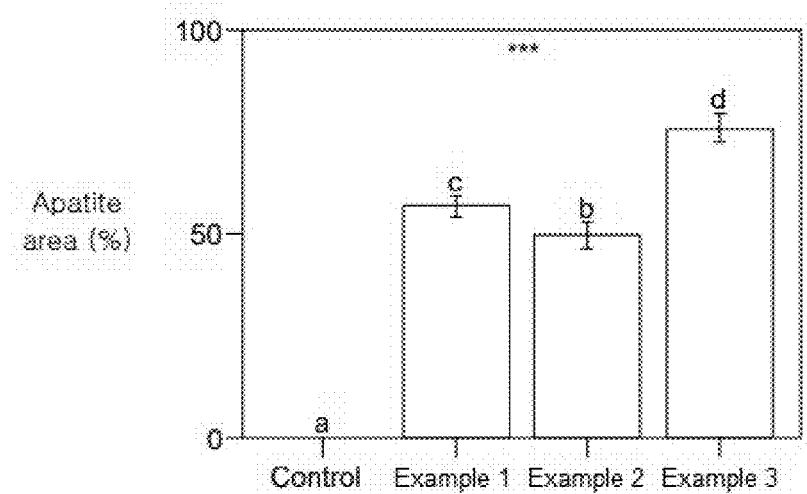

Furthermore, with reference to FIG. 7B, the Raman spectrum result for the bone activation ability in the examples of the present invention due to a zwitterionic material is shown. The intensity of the peak corresponding to $PO_4^{3-}$ at 984 $cm^{-1}$ is shown to be higher than that of the control in all of Examples 1 to 3 of the present invention, and among them, Example 3 is the intensity of the peak corresponding to $PO_4^{3-}$, which is the main component of apatite, is shown to be the highest. That is, by including the zwitterionic material, the formation of $PO_4^{3-}$ capable of mineralizing bone, i.e., teeth, may be improved, which may mean that in particular, when two or more kinds of zwitterionic materials are included in a specific ratio, the effect may be further enhanced.

Further, with reference to (b) of FIG. 7B in which the above-mentioned results are quantified, Examples 1 to 3 of the present invention show that the area of apatite is significantly higher than that of the control (p<0.001), and it is shown that the area of the apatite grown in the examples of the invention is 50 to 75 times higher than that of the control.

Figure 7C:
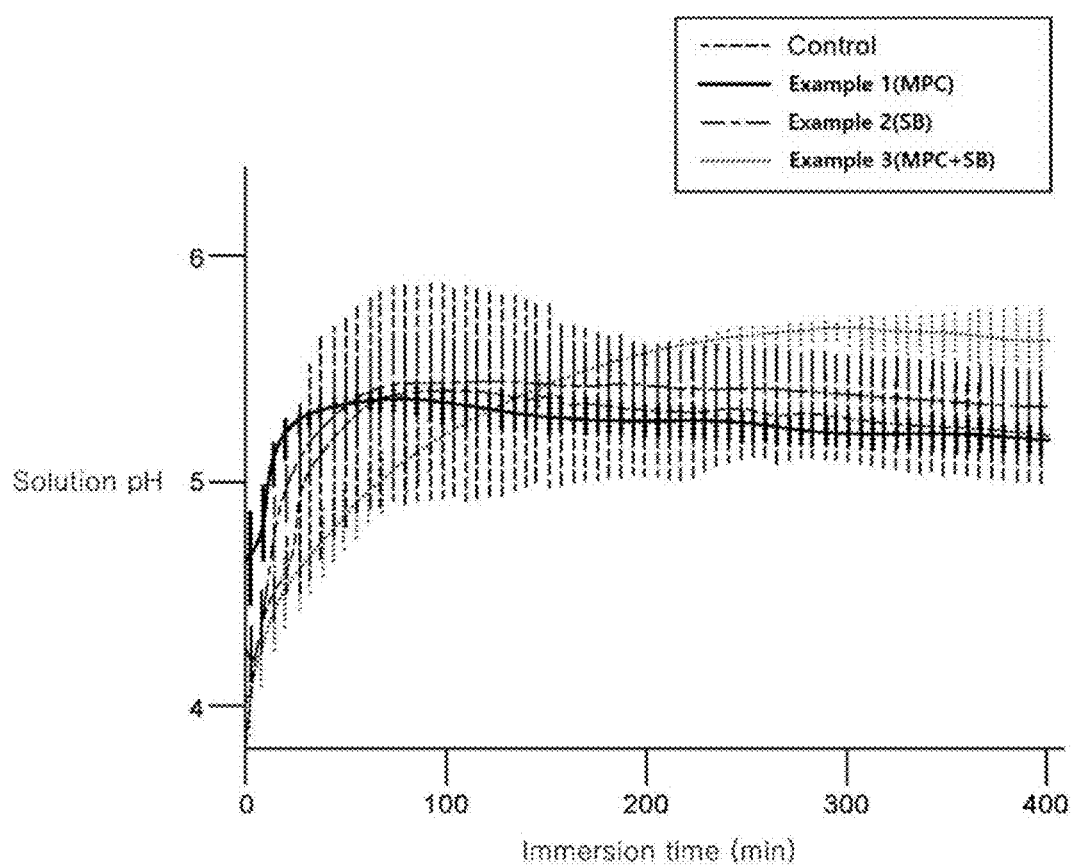
FIG. 7C shows the results for the change in pH of a dental glass ionomer cement composition according to one example of the present invention.

Furthermore, with reference to FIG. 7C, the results for the change in pH of a dental glass ionomer cement composition according to one example of the present invention are shown. In this case, in order to measure the change in pH of the dental glass ionomer cement composition according to one example of the present invention, the examples and the control were immersed in a lactic acid solution, and then the pH was measured over time and compared.

Teeth are composed of enamel, dentin, cementum, and pulp, and enamel is the hardest tissue in the outermost layer of teeth and includes hydroxyapatite, that is, $Ca_{10}(PO_4)_6(OH)_2$ as a main component. This enamel may be dissolved by acid. More specifically, since $Ca_{10}(PO_4)_6(OH)_2$ may be completely dissolved by hydrogen ions as shown in Formula 1 below, it may be easily dissolved in an acidic solution containing many hydrogen ions.

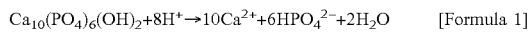

$$Ca_{10}(PO_4)_6(OH)_2 + 8H^+ \rightarrow 10Ca^{2+} + 6HPO_4^{2-} + 2H_2O \quad \text{[Formula 1]}$$

After all, in order to prevent dissolution of tooth enamel, that is, demineralization, pH in the teeth and oral cavity may be important.

Accordingly, with reference to FIG. 7C, Examples 2 and 3 of the present invention are shown to create a higher pH environment than the control after 150 minutes. That is, by including the zwitterionic material, Examples 2 and 3 of the present invention form a hydration layer due to the released amount of ions, that is, as the number of hydroxide (OH) ions increases, the pH thereof may be changed to basic. Accordingly, the present invention including the zwitterionic material may prevent acidification of the pH environment in teeth and oral cavity, thereby preventing demineralization of enamel.

From the above results, as the dental glass ionomer cement composition according to one example of the present invention includes a zwitterionic material, the release of ions related to bone formation, such as P and Ca, may be improved, so that in vivo activities such as immune cell induction and accordingly the chain mechanism are increased, and thus, the formation of an enamel, which is a very robust hard tissue at the outermost part of the tooth, may be promoted. Accordingly, the dental glass ionomer cement composition according to one example of the present invention may result in not only a simple antifouling effect and an antibacterial effect, but also fundamental treatment of teeth and functional improvement thereof. Accordingly, the dental glass ionomer cement composition according to one example of the present invention promotes the formation of an enamel layer, thereby protecting the pulp, which is a deep tissue such as cells, nerves, and blood vessels, which are formed in the tooth, from dental caries bacteria.

Hereinafter, with reference to FIG. 8, the wettability and mechanical properties of a dental glass ionomer cement composition according to one example of the present invention will be described. At this time, in order to evaluate the wettability and mechanical properties of the examples of the present invention and the control, compressive strength and wettability were measured. Furthermore, the measurement of compressive strength was performed in accordance with the international standard ISO 9917-1 (2017), and the examples of the present invention and the control used for measuring the compressive strength were prepared as cylindrical specimens having a diameter of 6 mm±0.1 mm and a height of 4 mm±0.1 mm, and a load was applied to fracture in a general-purpose testing machine at a crosshead speed of 1 mm/min in order to measure the compressive strength of the specimens. Furthermore, the compressive strength was calculated by the equation of $C=4p/(\pi)$ (wherein, p means the load, d means the diameter of the measured specimen, and C means compressive strength in MPa). Furthermore, the wettability measurement was performed by measuring the contact angle between the liquid and the solid surface when the liquid (water) is dropped on the solid surface and the liquid forms a droplet on the solid surface, and the examples and the control used in this case were prepared as disk-shaped specimens having a diameter of 15 mm and a thickness of 2 mm, and after dropping 3 μL of distilled water to each specimen, the contact angle thereof was measured.

Figure 8:
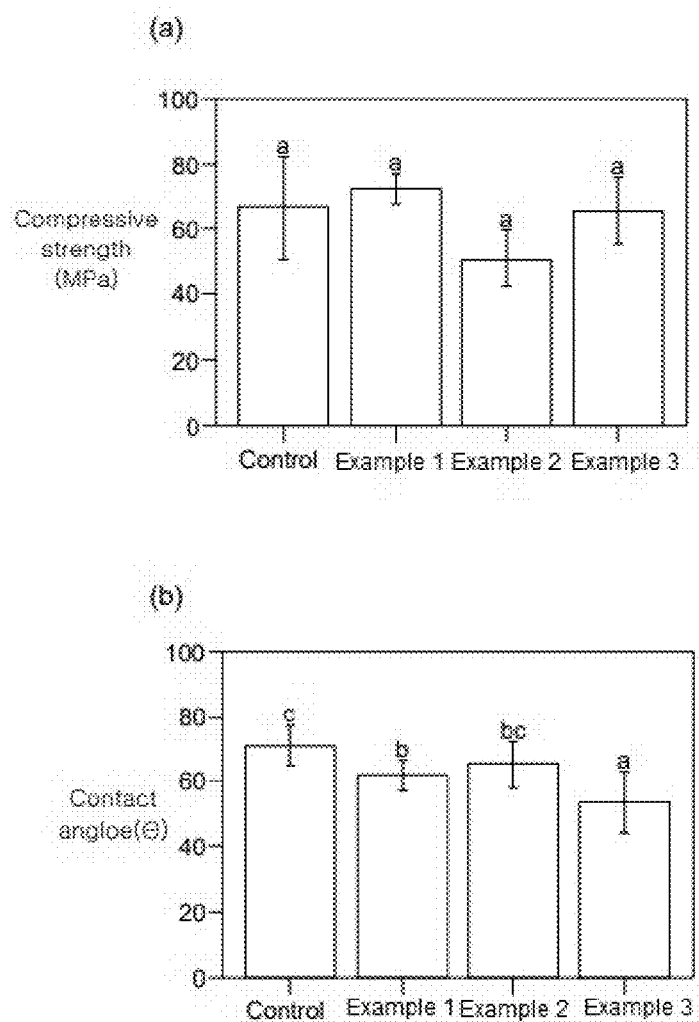
FIG. 8 shows the results for wettability and mechanical properties of a dental glass ionomer cement composition according to one example of the present invention.

First, with reference to (a) of FIG. 8, the compressive strength of the examples of the present invention and the control is shown to have 50 to 80 MPa with no difference. That is, due to the addition of the zwitterionic material, it may mean that the mechanical properties of the dental glass ionomer cement composition according to one example of the present invention are not changed or weakened.

Furthermore, with reference to (a) of FIG. 8, Examples 1 to 3 of the present invention are shown to have a contact angle significantly lower than that of the control (p<0.001), and in particular, Example 3 including two or more kinds of zwitterionic materials is shown to be statistically significant and have the lowest contact angle.

That is, due to the addition of the zwitterionic material, it may mean that the GIC may release more ions, and thus, the polarity increases and the hydrophilicity increases accordingly. This increase in hydrophilicity may mean a strong electrostatic interaction with water (hydrogen bonding), so that the dental glass ionomer cement composition according to one example of the present invention forms a hydration layer such as a thin film on teeth, thereby providing an antifouling effect that prevents the access of bacteria and the sticking of various contaminants.

Although the examples of the present invention have been described in more detail with reference to the accompanying drawings, the present invention is not necessarily limited to these examples, and various modifications may be made within the scope without departing from the technical spirit of the present invention. Therefore, the examples disclosed in the present invention are not intended to limit the technical spirit of the present invention, but to explain, and the scope of the technical spirit of the present invention is not limited by these examples. Therefore, it should be understood that the examples described above are illustrative and not restrictive in all respects. The protection scope of the present invention should be construed by the following claims, and all technical spirits within the equivalent range should be construed as being included in the scope of the right of the present invention.

What is claimed is:

1. A dental glass ionomer cement (GIC) composition comprising a zwitterionic material and a glass ionomer cement,
   wherein the zwitterionic material has a content of about 1 to 5 wt % based on the total mass of the dental glass ionomer cement composition,
   wherein the zwitterionic material comprises 2-methacryloyloxyethyl phosphorylcholine (MPC) and sulfobetaine methacrylate (SB), and
   wherein the MPC and SB are included in a weight ratio of 1:3 to 3:1.

2. The dental glass ionomer cement composition according to claim 1, wherein the dental glass ionomer cement composition further comprises one or more selected from the group consisting of hydroxylapatite (HAp), glass fiber, silver-tin alloy, zirconia ($ZrO_2$), alumina ($Al_2O_3$), titania ($TiO_2$) nanoparticles, and bioactive glass.

3. The dental glass ionomer cement composition according to claim 1, wherein the GIC has a content of about 95 to 99 wt % based on the total mass of the dental glass ionomer cement composition.

4. The dental glass ionomer cement composition according to claim 1, wherein the GIC comprises an acid-reactive inorganic filler powder and a liquid containing a poly acid.

5. The dental glass ionomer cement composition according to claim 4, wherein the poly acid comprises one or more selected from the group consisting of: homopolymers of acrylic acid, methacrylic acid, itaconic acid, maleic acid, glutaconic acid, aconitic acid, citraconic acid, mesaconic acid, fumaric acid or tiglic acid, and copolymers thereof; and a copolymer of maleic acid and ethylene.

6. The dental glass ionomer cement composition according to claim 4, wherein the liquid containing the poly acid further comprises itaconic acid.

7. The dental glass ionomer cement composition according to claim 4, wherein the acid-reactive inorganic filler powder comprises one or more selected from the group consisting of basic metal oxides, metal hydroxides, aluminosilicate glass, fluoroaluminosilicate glass, and calcium fluoroaluminosilicate glass.

8. The dental glass ionomer cement composition according to claim 4, wherein the acid reactive inorganic filler powder further comprises barium glass.

9. The dental glass ionomer cement composition according to claim 1, wherein the dental glass ionomer cement composition further comprises one or more selected from the group consisting of a stabilizer, a flame retardant, an antistatic agent, a softener, a modifier, a filler, a fluorescence brightening agent, a lubricant, an inclusion reducing agent, a polycondensation catalyst, a defoamer, an emulsifier, a thickener, and a perfume.

10. The dental glass ionomer cement composition according to claim 1, wherein the dental glass ionomer cement composition further comprises one or more adhesive materials selected from the group consisting of hydroxypropyl methylcellulose, hydroxyethyl cellulose, hydroxypropyl cellulose, polyvinyl alcohol, polyvinyl pyrrolidone, carbomer, and vinyl acetate resin.

11. The dental glass ionomer cement composition according to claim 1, wherein the dental glass ionomer cement composition comprises one or more functional groups selected from the group consisting of C=O, C—N, $N^+(CH_3)_3$, POCH, S=O symmetric, and S=O asymmetric.

12. The dental glass ionomer cement composition according to claim 1, wherein the dental glass ionomer cement (GIC) comprises one or more selected from the group consisting of Zn, Na, F, O, N, Ca, C, Cl, S, P, Si, and Al.

13. A method of preparing a dental glass ionomer cement composition, comprising the steps of:
mixing about 1 to 5 wt % of zwitterionic material in a liquid of glass ionomer cement (GIC) based on the total mass of the dental glass ionomer cement composition, and
mixing the liquid of glass ionomer cement (GIC) in which the zwitterionic material is mixed, and a powder of glass ionomer cement (GIC),
wherein the zwitterionic material comprises 2-methacryloyloxyethyl phosphorylcholine (MPC) and sulfobetaine methacrylate (SB), and
wherein the MPC and SB are included in a weight ratio of 1:3 to 3:1.

14. The method of preparing the dental glass ionomer cement composition according to claim 13, wherein the step of mixing the zwitterionic material comprises a step of mixing one or more selected from the group consisting of hydroxylapatite (HAp), glass fiber, silver-tin alloy, zirconia ($ZrO_2$), alumina ($Al_2O_3$), titania ($TiO_2$) nanoparticles, and bioactive glass.

* * * * *